US006297004B1

(12) United States Patent
Russell et al.

(10) Patent No.: US 6,297,004 B1
(45) Date of Patent: *Oct. 2, 2001

(54) RECOMBINANT VIRUSES DISPLAYING A NONVIRAL POLYPEPTIDE ON THEIR EXTERNAL SURFACE

(75) Inventors: Stephen J. Russell; Robert E. Hawkins; Gregory P. Winter, all of Cambridge (GB)

(73) Assignee: Cambridge Drug Discovery Holding, LTD, Cambridge (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/032,084

(22) Filed: Feb. 27, 1998

Related U.S. Application Data

(62) Division of application No. 08/381,960, filed as application No. PCT/GB93/01992 on Sep. 22, 1993, now Pat. No. 5,723,287.

(30) Foreign Application Priority Data

Sep. 22, 1992 (GB) .................................................... 9220010
Mar. 11, 1993 (GB) .................................................... 9304962

(51) Int. Cl.$^7$ ............................... C12Q 1/70; C12N 7/01; C12N 15/867

(52) U.S. Cl. ........................ 435/5; 435/235.1; 435/320.1

(58) Field of Search ................................. 435/5, 6, 235.1, 435/320.1; 536/23.4, 23.72

(56) References Cited

U.S. PATENT DOCUMENTS 5,714,316 * 2/1998 Weiner et al. ........................... 435/6
5,723,287 * 3/1998 Russell et al. ........................... 435/5

FOREIGN PATENT DOCUMENTS

| WO90/12087 | 10/1990 | (WO) . |
| WO92/05266 | 4/1992 | (WO) . |
| WO92/14829 | 9/1992 | (WO) . |
| WO93/00103 | 1/1993 | (WO) . |
| WO93/05147 | 3/1993 | (WO) . |
| WO93/14188 | 7/1993 | (WO) . |
| WO93/20221 | 10/1993 | (WO) . |

OTHER PUBLICATIONS

Baird et al., 1990, Mediation of Virion penetration into vascular cells by association of basic fibroblast growth factor with herpes simplex virus type 1, Nature.,48: 344–346.
Bass et al., 1990, Hormone Phage: An Enrichment Method fro Variant Proteins with Altered Binding Properties, Wiley–Liss, Inc.,8:309–314.
Battini et al., 1992, Receptor Choice Determinants in the Envelope Glycoproteins of Amphotropic, Xenotropic, and Polytropic Murine Leukemia Viruses, J. Virology 66:1468–1475.
Besmer et al., 1977, Mechanism of restriction of ecotropic and xenotropic murine leukemia viruses and formation of pseudotypes between the two viruses. J. Virology 21: 965–973.
Boulay et al., 1988, Posttranslational Oligomerization and Cooperative Acid Activation of Mixed Influenza Hemagglutinin Trimers, Journal of Cell Biology 106:629–639.
Briddon et al., 1990, Geminivirus Coat Protein Gene Replacement Alters Insect Specificity, Virology 177:85–94.
Bruhn et al., 1987, I The Occurrence of Falcarinol and Didehydrofalccarinol in Ivy, Natural Allergenes, 42b:1328–1332.
Canivet et al., 1990, Replication of HIV–1 in a Wide Variety of Animal Cells following Phenotypic Mixing with Murine Retroviruses, Virology178:543–551.
Copeland et al., 1998, Folding Trimerization, and Transport Are Sequential Events in the Biogenesis of Influenza Virus Hemagglutinin, Cell 53: 197–209.
Devaux et al., 1990, Structure of Adenovirus Fibre, J.Mol. Biol. 215: 567–588.
Devlin et al., 1990, Random Peptide Libraries: A source of Specific Protein Binding Molecules, Science 249:404–406.
Dolter et al., 1993, Incorporation of CD4 into Virions by a Recombinant Herpes Simplex Virus, J. Virology 67:189–195.
Doms et al., 1990, Human Immunodeficiency Virus Types 1 and 2 and Simian Immunodeficiency Virus env Proteins Possess a Functionally Conserved Assembly Domain, J. Virology 64:3537–3540.
Dong et al., 1992, A Chimeric Avain Retrovirus Containing the Influenza Virus Hemagglutinin Gene Has an Expanded Host Range, J. Virology 66:7374–7382.
Einfeld et al., 1988, Oligomeric structure of a prototype retrovirus glycoprotein,, Proc. Natl. Acad. Sci. 85:8688–8692.

(List continued on next page.)

Primary Examiner—Robert A. Schwartzman
(74) Attorney, Agent, or Firm—Kathleen M. Williams; Palmer & Dodge, LLP

(57) ABSTRACT

We have made retrovirus particles displaying a functional antibody fragment. We fused the gene encoding an antibody fragment directed against a hapten with that encoding the viral envelope protein (Pr80env) of the ecotropic Moloney murine leukemia virus. The fusion gene was co-expressed in ecotropic retroviral packaging cells with a retroviral plasmid carrying the neomycin phosphotransferase gene (neo), and retroviral particles with specific hapten biding activities were recovered. Furthermore the hapten-binding particles were able to transfer the neo gene and the antibody-envelope fusion gene to mouse fibroblasts. In principle, the display of antibody fragments on the surface of recombinant retroviral particles could be used to target virus to cells for gene delivery, or to retain the virus in target tissues, or for the construction of libraries of viral display packages.

23 Claims, 10 Drawing Sheets

OTHER PUBLICATIONS

Figure 1A:
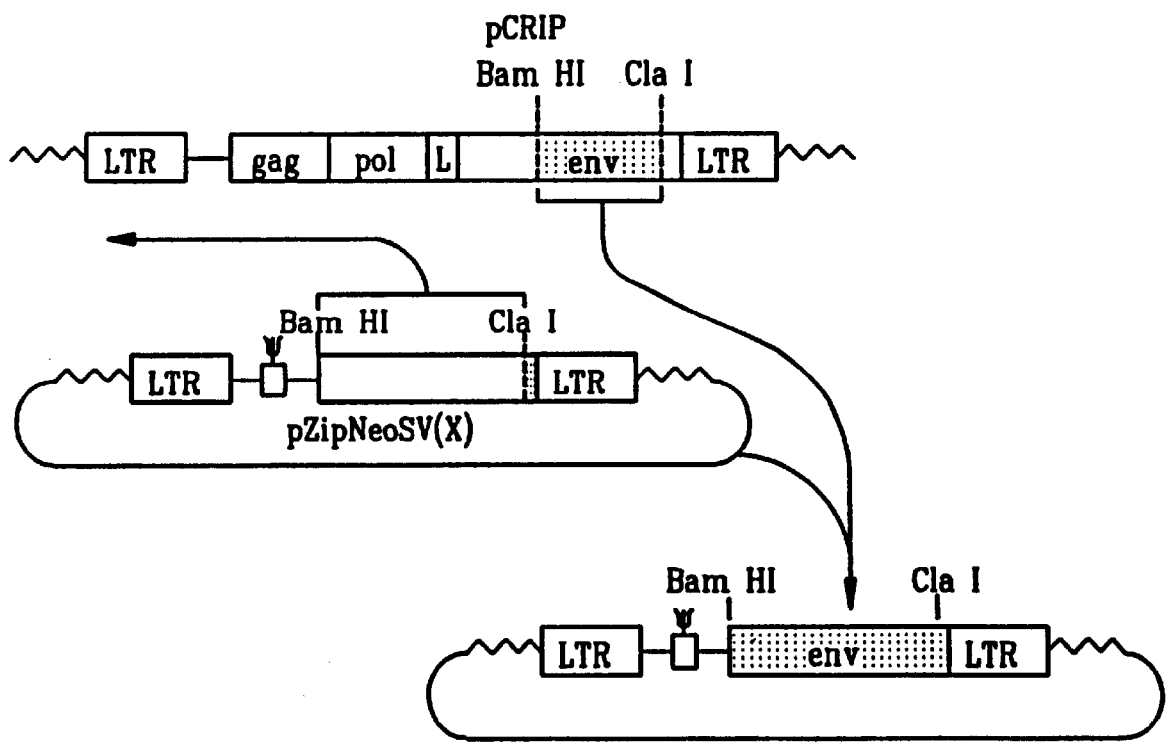

Etienne–Julan et al., 1992, The efficiency of cell targeting by recombinant retroviruses depends on the nature of the receptor and the composition of the artifical cell–virus linker, 73:3251–3255. J. Gen. Virol.

Goud et al., 1988, Antibody–Mediated Binding of a Murine Ecotropic Moloney Retroviral Vector to Human Cells Allows Internalization But not the Establishment of the Proviral State, Virology 163:251–254.

Harel et al., 1981, Cell Cycle Dependence of Synthesis of Unintegrated Viral DNA in Mouse Cells Newly Infected with Murine Leukemia Virus, Virology 110:202–207.

Holliger et al., 1993, Diabodies: Small bivalent and bispecific antibody fragments, Proc. Natl. Acad. Sci. 90: 6444–6448.

Hoogenboom et al., 1992, Human Antibodies from Synthetic Repertoires of Gemline VH Gene Segments Rearranged in Vitro, J. Mol. Biol. 227:381–388.

Kreis et al., 1986, Oligomerization Is Essential for Transport of *Vesicular Stomatitis* Viral Glycoprotein to the Cell Surface, Cell 45:929–937.

Levy ., 1977, Murine Xenotropic Type C Viruses, Virology 77: 811–825.

Lobel et al., 1984, Construction of Mutants of Moloney murine Leukemia virus by suppressor–linker insertional mutagenesis: Positions of viable inseration mutations, Proc. Natl. Acad. Sci. 81:4149–4153.

London et al., 1992, Infectious enveloped RNA virus antigenic chimeras, Proc. Natl. Acad. Sci. 89: 207–211.

Lusso et al., 1990, Expanded HIV–1 Cellular Troppism by Phenotypic Mixing with Murine Endogenous Retroviruses, Science, 247:848–852.

Mady et al., 1991, Antibody Dependent Enhancement of Dengue Virus Infection Mediated By Bispecific Antibodies Aganist Cell Surface Molecules Other Than Fcy Receptors, J. Immunology 147:3139–3144.

Mann et al., 1983, Construction of a Retrovirus Packaging Mutant and Its Use to Produce Helper–Free Defective Retrovirus, Cell, 33: 153–159.

Marks et al., 1991, Human Antibodies from V–gene Libraries Displayed on Phage, J. Mol. Biol. 222: 581–597.

Marsh et al., 1983, Virus Entry Into Animal Cells, Advances in Virus Research, 36: 107–151.

Mason et al., 1993, Antibody–Comlexed Foot–and–Mouth Disease Virus, but not Poliovirus, Can Infect Normally Insusceptible Cells via the Fc Receptor, Virology, 192: 568–577.

McCaffeerty et al., 1990, Phage Antibodies: Filamentous phage displaying antibody variable domains, Nature, 348: 552–554.

Metsikko et al., 1989, Role of Heterrologous and Homologous Glycoproteins in Phenotypic Mixing Between Sendi Virus Vesicular Stomatitis Virus, J. Virology 63:5111–5118.

Mullis et al., 1990, Relative Accessibility of N–Aceetyglucosaamine in Trimers of the Adenovirus Types 2 and 5 Fiber Proteins, J. Virology 64: 5317–5323.

Neda et al., 1991, Chemical Modification of an Ecotropic Murine Leukemia Virus Results in Redirection of Its Target Cell Specificity, J. Biology Chemistry 266:14143–14146.

Parmley et al., 1988, Antibody–selectable filamentous fd phage vectors: affinnnity purification of target genes, Gene 73:305–318.

Pinter et al, 1978, The Nature of the Association between the Murine Leukemia Virus Envelope Proteins, Virology 91:345–351.

Polonoff et al, 1982, Glycosylation and Intracellular Transport of Membrane Glycoproteins Encoded by Murine Leukemia Viruses, J. Biological Chemistry 257:14023–14028.

Porterfield et al., Antibody–Dependent Enhancement of Viral Infectivity, Advance in Virus Research 31:335–355. 1986.

Rose et al., 1991, Poliovirus Antigen Chimeras, Tibtech 9: 415–421.

Roux et al., 1989, A versatile and potentially general approach to the targeting of specific cell types by retrrroviruses: Application to the infection class I and class II antigens by mouse ecotropic murine leukemia virus–derived viruses, Proc. Natl. Acad. Sci. 86:9079–9083.

Ruigrok et al., 1990, Structure of Adenovirus Fibre, J. Mol. Biol. 215:589–596.

Schnitzer et al., 1977, Pseudotypes of *Vesicular Stomatitis* Virus with the Envelope properties of Mammalian and Primate Retroviruses, J. Virology 23:449–454.

Schols et al., 1992, Presence of Class II Histocompatibilty DR Proteins on the Envelope of Human Immunodeficiency Virus Demonstrrated by FACS Analysis, Virology 189:374–376.

Schubert et al., 1992, Insertion of the Human Immunodeeficiency Virus CD4 Receptor into the Envelope of *Vesicular Stomatitis* Virus Particles, J. Virology 66:1579–1589.

Shinnick et al., 1981, Nucleotide sequence of Moloney Murine Leukaemia virus, Nature 293:543–548.

Shoemaker et al., 1980, Structure of a cloned circular Moloney murine leukemia virus DNA molecule containing an inverted segment: Implications for retrovirus integration, Proc. Natl. Acad. Sci. 77:3932–3936.

Smith al., 1985, Filamentous Fusion Phage: Novel Expression Vectors That Display Cloned Antigens on the Virion Surface, Science 228:131–1317.

Spector et al., 1990, Human Immunodeficiency Virus Pseudotypes with Expanded Cellular and Species Tropism, J. Virology 64:2298–2308.

Stengelin et al., 1988, Isolation of DNAs for two distinct human Fc receptors by ligand affiinity cloning, EMBO Journal 7: 1053–1059.

Weiss et al., 1977, Phenotypic Mixing between Avian and Mammalian RNA Tumor Viruses: I Envelope Pseudotypes of *Ruos Sarcoma* Virus, Virology 76:826–834.

Wilson et al., 1989, Formation of Infections Hybrid Virions with Gibbon Ape Leukemia Virus and Human T–Cell Leukemia Virus Retroviral Envelope Glycoproteins and the gag and pol Proteins of Moloney Murine Leukemia Virus, J. Virology 63:2374–2378.

Young et al., 1990, Efficient Incorporation of Human CD4 Protein into Avian Leukosis Virus Particles, Science 450:1421–1423.

* cited by examiner

FIG. 3

| coating — | uncoated | uncoated | NIP.BSA | NIP.BSA | NIP.BSA | NIP.BSA |
| --- | --- | --- | --- | --- | --- | --- |
| virus — | NIPenv5 | NIPenv5 | NIPenv5 | DCNeo | NIPenv5 | DCNeo |

| coating — | uncoated | uncoated | Ox.BSA | Ox.BSA | Ox.BSA | Ox.BSA |
| --- | --- | --- | --- | --- | --- | --- |
| virus — | DCNeo | DCNeo | NIPenv5 | DCNeo | NIPenv5 | DCNeo |

FIG. 5

RECOMBINANT VIRUSES DISPLAYING A NONVIRAL POLYPEPTIDE ON THEIR EXTERNAL SURFACE

This application is a division of Ser. No. 08/381,960 filed May 3, 1995 U.S. Pat. No. 5,723,287 which is a 371 of PCT/GB93/01992 filed Sep. 22, 1993.

FIELD OF INVENTION

This invention relates to recombinant viruses, also referred to as recombinant viral particles. By "recombinant virus", we mean a virus in which at least one of the components of the virion particle is altered or derived by recombinant DNA technology.

This invention also relates to the field of therapeutic gene transfer and concerns the teleological design and use of vectors to derive recombinant proteins or protein components suitable for display on the surface of a gene delivery vehicle which, when displayed on the surface of the gene delivery vehicle, through their interaction with components of the surface of a eukaryotic target cell, are capable of influencing the efficiency with which the gene delivery vehicle delivers its nucleic acid into the target cell, or of transmitting a signal to the target cell which influences the subsequent fate of the delivered nucleic acid, and which are thereby capable of enhancing the suitability of the gene delivery vehicle for an intended application.

BACKGROUND TO THE INVENTION

Display of a Functional Nonviral Polypeptide on a Virus which can Infect Eukaryotic Cells Recombinant viruses have been widely used as vectors for the delivery of foreign genes into eukaryotic cells. Recombinant viruses which are used for delivery of foreign genes to animal cells include members of several virus families, including Adenovirus, Herpesvirus, Togavirus, and Retrovirus families. Viruses which infect eukaryotic cells comprise a protein shell or shells (the capsid) formed by the multimeric assembly of multiple copies of one or more virus-encoded proteins. The capsid houses the viral nucleic acid (RNA or DNA) and may or may not be enveloped in a lipid bilayer which is studded with virus-encoded oligomeric spike glycoproteins, visible on electron micrographs as spikes projecting from the surface of the virus.

The initial event in the virus life cycle is binding to the surface of the eukaryotic target cell. Binding is mediated by the direct interaction of specialised proteins or glycoproteins on the surface of the virus (antireceptors) with receptors on the surface of the target cell, or indirectly via soluble ligands which bind the virus to receptors on the surface of the target cell. In some instances, the interaction between a virus and a target cell receptor may transmit a metabolic signal to the interior of the target cell. Binding is followed by penetration of the target cell membrane and entry of the viral nucleic acid into the cytosol (reviewed in Marsh and Helenius 1989 Adv Virus Res 36 p107–151). Some nonenveloped viruses undergo conformational changes which result in their direct translocation across the target cell membrane, whereas others, such as adenovirus, are first endocytosed and then cause disruption of the wall of the acidified endosomal vesicle. Enveloped viruses fuse with the target cell plasma membrane whereupon the virus capsid (or core particle), housing the viral nucleic acid is released into the cytoplasm of the target cell. This envelope fusion event is catalysed by oligomeric viral membrane spike glycoproteins which are anchored in the viral envelope and may, or may not be dependent on the prior endocytosis of bound virus and its exposure to an acidic environment within the endosomal vesicle. The mechanisms by which viral spike glycoproteins catalyse membrane fusion may involve their proteolytic cleavage, the dissociation of noncovalently linked subunits or other conformational alterations which expose buried hydrophobic moieties capable of penetrating the lipid membrane of the target cell. Thus, virus-mediated delivery of nucleic acid is a complex, multistage process.

After delivery of the viral nucleic acid into the target cell, further steps in the viral life cycle which lead to viral gene expression, genome replication and the production of progeny viruses are often critically dependent on variable host cell factors. For example, division of the infected target cell is required for efficient integration of a reverse-transcribed retroviral genome into the host cell chromosome and subsequent retroviral gene expression (Harel et al, 1981 Virology 110 p202–207).

The spike glycoproteins of one virus can be incorporated into the viral particles of another strain. Thus with dual viral infection of a single cell by two enveloped mammalian viruses, the host range of either virus may be predictably extended due to promiscuous incorporation of spike glycoproteins encoded by both viruses. This has been shown for closely or distantly related retroviruses (Levy, 1977 Virology 77 p811–825; Weiss and Wong, 1977 Virology 76 p826–834; Besmer and Baltimore, 1977 J Virol 21 p965–973; Canivet et al, 1990 Virology 178 p543–541; Lusso et al, 1990 Science 247 p848–852; Spector et al, 1990 J Virol 64 p2298–2308) and for unrelated viruses from different families (Schnitzer et al, 1977 J Virol 23 p449–454; Metsikko and Garoff, 1989 J Virol 63 p5111–5118; Schubert et al, 1992 J Virol 66 p1579–1589). The spike glycoproteins of certain closely or distantly related retroviruses have also proved to be entirely interchangable, allowing production of infectious hybrid virions with envelope spike glycoproteins of one retrovirus and core particles of another retrovirus (Mann et al, 1983 Cell 33 p153–159; Wilson et al, 1989 J Virol 63 p2374–2378). Similar results have been demonstrated with insect/plant viruses (Briddon et al, 1990 Virology 177 p85–94). Furthermore virus host range was predictably altered by exchanging the N-terminal receptor binding domains of envelope spike glycoproteins from related retroviruses with distinct cellular tropisms (Battini et al, J Virol 1992:66 p1468–1475). When viral spike glycoproteins from closely related virus strans were coexpressed in the same cell, mixed oligomers were formed with high efficiency (Boulay et al, 1988 3 Cell Biol 106 p629–639; Doms et al, 1990 J Virol 64 p3537–3540). Thus, there is considerable scope for altering the host ranges of recombinant viruses by exchanging, mixing and recombining the viral spike glycoproteins of naturally occurring viruses.

However, a relatively small minority of the universe of eukaryotic cell surface structures are actually used as receptors by naturally occurring viruses and it is often difficult to identify a virus with a host range which coincides with the requirements of a particular gene therapy application. For example, to genetically modify a population of normally quiescent haemopoietic stem cells in vivo, a most desirable gene transfer vehicle would be a recombinant retrovirus whose spike glycoproteins do not bind to nontarget cells, but which bind to haemopoietic stem cells and mediate membrane fusion and which also signal the target cell to divide as the nucleic acid is delivered. There are no known naturally occurring viral spike glycoproteins which meet these requirements, and there is therefore a need for new technologies to facilitate the generation of novel spike glycoproteins which can enhance the specificity and efficiency of virus-mediated gene delivery and expression.

Preformed viral particles can be attached to cells which lack virus receptors by way of a (multivalent) molecular bridge. This is clearly demonstrated by the phenomenon of antibody-dependent enhancement of viral infectivity. Thus, antibody-complexed foot-and-mouth disease virus (a nonenveloped picornavirus) has been shown to infect normally insusceptible cells via the Fc receptor (Mason et al, 1993 Virology 192 p568–577). The phenomenon of antibody-dependent enhancement of viral infectivity, mediated through binding of antibody-complexed viruses to cellular Fc receptors and complement receptors has been demonstrated for several enveloped and nonenveloped viruses (Porterfield, 1986 Adv Virus Res 31 p335–355). Moreover, bivalent antibodies that bind dengue virus to cell surface components other than the Fc receptor were recently shown to enhance infection (Mady et al, 1991 J Immunol 147 p3139–3144). Also, Baird et al (1990 Nature 348 p344–346) showed that herpes simplex virion penetration into vascular cells via the basic fibroblast growth factor (FGF) receptor requires the association of soluble FGF with the viral particles.

Goud et al, (1988 Virology 163 p251–254) incubated ecotropic murine leukaemia viruses (MLVs) with monoclonal antibodies against the gp70SU viral envelope spike glycoprotein and incubated human HEp2 cells with monoclonal antibodies against the transferrin receptor. Crosslinking of the bound monoclonal antibodies with a sheep anti-mouse kappa light chain antibody allowed the binding of virus on HEp2 cells and its subsequent internalisation into the cells at 37° C. However, internalisation of the virus by this route was not followed by establishment of the proviral state.

Subsequently, Roux et al (1989 Proc Natl Acad Sci USA 86 p9079–9083) and Etienne-Julan et al (1992 J Gen Virol 73 p3251–3255)) used a similar approach in which biotinylated antibodies against the murine ecotropic retroviral envelope spike glycoprotein and against specific membrane markers expressed on human cells were bridged by streptavidin and used to link the virus to the human host cell. The method was successfully used to infect human cells with ecotropic murine retroviruses bound to MHC class I and class II antigens, and to the receptors for epidermal growth factor and insulin. However, targeting of the transferrin, high density lipoprotein and galactose receptors, and of various membrane glycoconjugates, by murine ecotropic retroviruses did not lead to the establishment of a proviral state.

Preformed viral particles can also be chemically modified to facilitate their binding to target cells which lack receptors for the unmodified virus (Neda et al, 1991 J Biol Chem 266 p14143–14149). Murine ecotropic retroviral particles which had been chemically modified with lactose were shown to bind specifically to the asialoglycoprotein receptor on human HepG2 cells (which lack receptors for murine ecotropic viruses). Binding was followed by retroviral infection of the human cells as indicated by transfer of a functional β-galactosidase gene.

Thus, the display of a functional non-viral polypeptide at the surface of the virus can lead to the preferential binding of the modified viral particles to selected target cells, and in some cases, dependent on the exact specificity of the displayed polypeptide, binding is followed by delivery and expression of the encapsidated viral nucleic acid. However, the present inventors realised that a method for the production of viral particles which incorporate and display a nonviral polypeptide during their assembly would be more useful, avoiding the need for modification of preformed virions Such a method would also facilitate the use of such recombinant viruses as genetic display packages (see below).

Non-viral proteins have been incorporated, during assembly, into viral particles capable of infecting eukaryotic cells. Thus, spontaneous incorporation of non-virus-encoded mammalian cellular proteins has been observed in retroviral particles. For example, MHC antigens are incorporated into the envelopes of human and simian immunodeficiency viruses (Gelderblom et al, 1987 Z Naturforsch 42 p1328–1:334; Schols et al, 1992 Virology 189 p374–376). Also, mammalian CD4 expressed in avian (quail) cells was incorporated into the envelopes of budding avian retroviruses (Young et al, 1990 Science 250 p1421–1423). Viral incorporation and display of CD4 was also demonstrated in recombinant herpes simplex virions constructed by inserting the CD4 gene into the HSV-1 genome under the control of a viral promoter (Dolter et al, 1993 J Virol 67 p189–195). However, nonviral proteins are generally excluded from assembling viral particles, or incorporated very inefficiently. The present inventors believe a more reproducible strategy for the efficient incorporation and display of nonviral polypeptides on viruses which can infect eukaryotic cells would be to fuse the nonviral polypeptide to a viral component, such as a viral spike glycoprotein, which carries a signal for incorporation into the viral particle.

The nucleic acid sequences encoding a nonviral peptide or polypeptide can be linked, without disruption of the translational reading frame, to nucleic acid sequences coding for all or part of the gene III protein of filamentous bacteriophage, thereby creating a hybrid gene encoding a chimaeric gene III protein (McCafferty et al, 1990 Nature 348 p552–554; Smith, 1985 Science 228 p1315–1317; Parmley and Smith, 1988 Gene 73 p305–318; Scott and Smith, 1990 Science 249 p404–406). The details of the construction can be varied such that the gene III moiety of the chimaeric protein remains substantially intact or is lacking one or more domains. When expressed in prokaryotic cells which are shedding filamentous bacteriophage, the chimaeric gene, III protein is incorporated into a proportion of the progeny phage and those phage display the chimaeric protein on their surface. Incorporation of the chimaeric protein is presumed to occur during phage assembly through the specific interaction of the C-terminal gene III moiety of the chimaeric protein with other protein components of the phage particle. Correct folding and function of the nonviral polypeptide moiety of the incorporated chimaeric gene III protein is apparent from the altered binding specificity of the phage particles, which corresponds with the binding specificity of correctly folded nonviral polypeptide moiety. It is possible to generate phage particles incorporating a combination of wild type and chimaeric gene III protein or incorporating exclusively the chimaeric gene III protein.

However, bacteriophage do not infect eukaryotic cells and cannot therefore be employed as gene delivery vehicles for such cells. Nor can they be used for the display of glycoproteins since their bacterial hosts lack the necessary enzymatic machinery for correct glycosylation of polypeptides.

In the case of nonenveloped viruses which can infect eukaryotic cells, initial binding to the target cell is mediated by the viral capsid which is composed of a multimeric symmetrical array of virus-encoded capsid proteins. Short (up to 26 aminoacids) nonviral peptides have been displayed on the surface of nonenveloped polioviruses by replacing surface-exposed polypeptide loops (up to 9 aminoacids) in the capsid proteins (Rose and Evans, 1991 Trends Biotech 9 p415–421). This was achieved by genetic manipulation and subsequent transfection of a full-length infectious cDNA clone of the RNA genome. The display of peptides in poliovirus antigen chimaeras has been pursued with a view to using the chimaeric particles as antigen presentation vehicles to stimulate immune responses against the displayed peptide in vaccinated animals or humans and for use as diagnostic reagents in serodiagnosis. Larger, functional, folded polypeptides have not been displayed on the outer surface of nonenveloped viruses which can infect eukaryotic cells.

In the case of all enveloped viruses and certain nonenveloped viruses (eg adenovirus) which can infect eukaryotic cells, initial binding to the target cell is mediated by specialised multifunctional, oligomeric spike glycoproteins rather than by simple unglycosylated monomeric proteins such as the gene III protein of filamentous bacteriophage. Thus, it is not possible simply to extrapolate from the bacteriophage gene III display system in the design of chimaeric variants of these oligomeric spike glycoproteins for incorporation into assembling virus particles and display of functional nonviral polypeptides at the surface of the virion. Correct glycosylation and oligomerisation of the spike glycoproteins of enveloped viruses is often required for successful transport to the cell surface and incorporation into viral particles (Polonoff et al, 1982 J Biol Chem 257 p14023–14028; Enfield and Hunter, 1988 Proc Natl Acad Sci USA 85 p8688–8692: Kreis and Lodish, 1986 Cell 46 p929–937; Copeland et al, 1988 Cell 53 p197–209). Proteolytic cleavage of assembled oligomeric viral spike glycoproteins frequently occurs during their transport through the Golgi apparatus to the cell surface. Thus, trimeric Murine Leukaemia Virus envelope glycoprotein precursors are proteolytically cleaved in the Golgi apparatus into p15TM transmembrane and gp70SU surface components, and these components are held together by noncovalent interactions or by covalent disulphide bonds (Pinter et al, 1978 Virology 91 p345–351).

Non-viral polypeptides have been displayed on a retrovirus by fusion to the membrane anchor sequence of the retroviral spike glycoprotein. Adopting this strategy, incorporation of chimaeric CD4-envelope proteins was demonstrated by immunoprecipitation of purified retroviral (RSV) particles, but there was no evidence for correct folding or function of the CD4 (Young et al, 1990 Science 250p11421–1423). Chimaeric VSV-G proteins comprising the cytoplasmic and transmembrane anchor domains of VSV-G spike glycoprotein fused to the ectodomain of CD4 were incorporated into the envelopes of infectious VSV particles (Schubert et al, 1992 J Virol 66 p1579–1589). However, the authors were not able to demonstrate correct folding or function of the virally incorporated CD4 and state that "Numerous experiments to demonstrate a specific tropism for HIV envelope-expressing cells were not successful so far. In the environment of a viral membrane, the receptor may not be functional".

The technique of insertional mutagenesis has been used to define domains of the MoMLV genome which are amenable to small alterations without deleterious effects on the virus (Lobel and Goff, 1984 Proc Natl Acad Sci USA 81 p4149–4153). Viable linker insertions in the env gene of an infectious molecular clone of MoMLV (eg in-6438-12 and in-7407-9) were shown to generate infectious retroviruses whose spike glycoproteins had presumably incorporated the four-residue nonviral peptide encoded by the inserted linker. However, no attempt was made to demonstrate display of such a peptide, nor was the possibility of surface display mentioned.

The present inventors have devised a novel strategy for the incorporation and display of nonviral polypeptides in fusion with viral glycoproteins, particularly oligomeric viral spike glycoproteins. The nucleic acid sequences encoding a nonviral polypeptide are fused, without disruption of the translational reading frame, to nucleic acid sequences coding for the oligomeric viral spike glycoprotein. The hybrid gene codes for a chimaeric glycoprotein in which the domain structure and organisation of the viral spike glycoprotein moiety remain substantially intact so as to conserve the post-translational processing, oligomerisation, viral incorporation and, possibly, fusogenic activities. The nonviral polypeptide is fused close to the terminus of the mature spike glycoprotein which is known to be displayed distally on the outside of the viral particle. To avoid possible steric hindrance between the nonviral polypeptide moieties which could significantly inhibit oligomerisation, the chimaeric glycoprotein can be expressed in virus-shedding cells in the presence of the wild-type virus spike glycoprotein such that each oligomeric unit need incorporate only a single copy of the chimaeric glycoprotein. Adopting this strategy, we have demonstrated incorporation of a chimaeric glycoprotein comprising a single chain antibody fused to a retroviral spike glycoprotein into murine ecotropic and amphotropic retroviral (MLV) particles. Moreover, in contrast to previous studies we have been able to demonstrate that the virally incorporated single chain antibody remains functional as evidenced by its ability to bind specifically lo its target antigen (NIP).

A logical extension of these studies is the construction of vectors of similar design for the display of nonviral peptides, polypeptides and glycopolypeptides other than single chain Fv antibody fragments on retroviral particles. Among the polypeptides and glycopolypeptides suitable for display on the particles are Fv and Fab antibody fragments, T-cell receptors, cytokines, growth factors, enzymes, cellular adhesion proteins such as integrins and selecting, Fc receptors etc. There is no reason why two or more different nonviral polypeptides should not be incorporated into a single virus particle by their co-expression as fusion proteins in the same packaging cell. The display of nonviral peptides, polypeptides or glycopolypeptides as similar fusions with the oligomeric spike glycoproteins of other retroviruses and with viruses of other families also follows directly from the this invention. Animal viruses of the Adenovirus, Togavirus, Rhabdovirus, Paramyxovirus, Orthomyxovirus and Retrovirus families which have relatively well-defined oligomeric spike glycoproteins are particularly suitable for such manipulation.

The invention, in one aspect, thus provides a recombinant viral particle capable of infecting eukaryotic cells, comprising a non viral polypeptide fused to a substantially intact viral glycoprotein or chimera of viral glycoproteins and a displayed on the external surface of the particle.

The term "viral glycoprotein" means a glycoprotein encoded by a virus in its natural state. The viral glycoprotein is typically a viral spike glycoprotein, i.e. a protein which in its natural state:

1. projects from the surface of the virus to be visible by electron microscope;
2. is oligomeric, having 2 to 6 subunits which may be identical or non identical, i.e. homo or heterooligomers;
3. is glycosylated;

4. comprises a structural signal which directs its efficient incorporation into the viral particle.

The chimera of viral glycoproteins must be capable of incorporation into the viral particle to satisfy conditions 1 to 4 above. One example of such a chimera is a protein comprising the transmembrane and cytoplasmic domains of the trimeric Rous Sarcoma Virus envelope glycoprotein fused to the trimeric extraviral domains of the influenza haemagglutinin (Dong et al., 1992 J. Virol. 66, 7374–7382).

The virus is conveniently a retrovirus, but this is not critical.

The eukaryotic cells are typically mammalian, e.g. human.

The polypeptide and glycoprotein are fused together, i.e. in the form of a single, continuous polypeptide chain.

It is important that the viral glycoprotein is substantially intact, i.e. retains all its domains, to conserve the post-translational processing, oligomerisation, viral incorporation and, possibly, fusogenic activities. However, certain alterations, e.g. mutations, deletions, additions, can be made to the glycoprotein which do not significantly affect these functions, and glycoproteins with such modifications are considered substantially intact.

The non viral polypeptide is preferably fused close to the terminus of the mature glycoprotein which is known to be displayed distally on the outside of the viral particle, so that folding of the distal terminal domain is not significantly disturbed.

The non viral polypeptide generally comprises at least 6 amino acids, and may range from a short polypeptide to a fully functional protein. The polypeptide may be glycosylated. The polypeptide typically comprises an antibody or antibody fragment, receptor, enzyme etc.

The non viral polypeptide can be selected to bind to a target eukaryotic cell, via a cell surface molecule, with the virus delivering encapsidated nucleic acid to the target cell. The viral particles of the invention thus find application in targeted gene delivery and targeted virotherapy, as will be discussed in more detail below.

The non viral polypeptide conveniently comprises antibody or antibody fragments e.g. heavy and light chain variable domains of an antibody, which may comprise framework regions homologous to the framework regions of human antibodies. Such variable domains are conveniently derived from phage display libraries, e.g. by being selected for binding to cell surface molecules.

Antibody fragments of low immunogenicity and peptides with desirable binding activities may be most versatile targeting agents for incorporation into particles for targeting human cells. Antibody fragments could be expressed as single chain fragments (in which the heavy and light chain variable domains are located on the same polypeptide, using by a flexible peptide linking the two domains directly) or as two chain constructs, in which one chain is fused to the second polypeptide and the other is secreted and associates with the fusion protein. Other possibilities for targeting the virus to the cell surface include cytokines, for example EGF for tumours with high expression, or T-cell receptors cloned from tumour-specific T cells.

For targeted binding, for example to human tumour cells, the virus particles should ideally not bind to other human cells. The non viral polypeptide should therefore confer novel (e.g. antitumour) binding activity on the particle. It is therefore desirable to use viral particles which do not naturally bind to the target cells, or which have been modified to destroy natural binding to the target cells. In this case, all binding to target cells will be attributable to the non viral polypeptide.

The target cell specificity of such binding may be further enhanced where two or more novel (e.g. antitumour) binding activities are displayed on a single particle. The viral particle may thus include one or more additional viral coat proteins, in addition to the fusion protein. Such additional proteins may or may not bind to the target cells and may or may not allow infection of the target cells. Additional binding activities conferred by the non viral polypeptide or viral protein moiety of the fusion protein or by unmodified coat proteins may decrease the specificity of binding to the tumour cells, and it will therefore often be desirable to choose these proteins to give minimal background or to inactivate their binding activity, for example by site directed mutagenesis.

After virus binding, fusion with or translocation across the limiting membrane of the target cell, sometimes preceded by endocytosis, is a necessary step which may require inclusion of specific (e.g. fusogenic) proteins in the coat of the viral particle (and these proteins should ideally not increase the background binding to nontarget cells). For example, inclusion of fusogenic influenza haemagglutinin trimers, mutated to destroy sialic acid receptor binding activity, could trigger low pH-dependent membrane fusion of endocytosed virus with the endosomal membrane. Where the nonviral polypeptide is fused to a viral coat protein, the coat protein moiety may itself carry the necessary fusogenic or translocating capability.

Viruses which Infect Eukaryotic Cells as Genetic Display Packages

The isolation of genes encoding proteins with known binding properties has recently been facilitated by selection technologies utilising genetic display packages. The genes encoding the protein are packaged such that the encoded protein is displayed on the outside of the package. The package is then selected by its binding affinity (for example an encoded antigen by binding to solid phase antibody), and replicated. The tight linkage between genes and encoded protein allow packages to be selected in rounds of binding and amplification, leading to selection factors of more than one in a million. Replicable packages have included mammalian cells—used to isolate the genes encoding lymphocyte surface markers from cDNA libraries (Strengelin S et al, 1988 EMBO J 7 p 1053–1059)—and filamentous bacteriophage—used to isolate the genes encoding antibody fragments (McCafferty et al, 1990 Nature 348 p552–554) and other proteins (Bass et al. 1990 Proteins: Struct Funct Genet 8 p309–314). The use of filamentous bacteriophage has even led to strategies for building antibodies in bacteria and improving their binding affinities, and so by-passing immunisation (Marks et al, 1991 J Mol Biol 222 p581–597; Hoogenboom and Winter, 1992 J Mol Biol 227 p381–388).

Viruses which are capable of infecting eukaryotic cells have not previously been used as genetic display packages to facilitate selection technologies. A typical DNA construct suitable for the generation and selection of a library of such genetic display packages should be small enough to allow convenient manipulation and would preferably comprise:

(1) A eukaryotic cell expression cassette whose encoded polypeptide comprises a structural signal to direct its efficient incorporation into viral particles and a nonviral moiety (peptide or polypeptide) which is displayed at the surface of the virion. For certain of the novel selection strategies proposed below the polypeptide should not include displayed viral moieties which bind to receptors present on the chosen target cells.

(2) Unique, noncomplementary restriction sites flanking the sequences which encode the nonviral moiety to facilitate the cloning of a diverse library of peptide or polypeptide sequences into this site.

(3) An viral encapsidation signal sequence to direct the incorporation of the sequences encoding the displayed polypeptide into the viral particles before they leave the packaging cell.

(4) Cis-acting sequences which, in the presence of appropriate transacting factors, mediate amplification of the copy number of the nucleic acid sequences which code for the displayed polypeptide and associated encapsidation signal sequence.

(5) A bacterial plasmid origin of replication and antibiotic resistance marker gene to facilitate amplification of the plasmid in a bacterial host strain (eg *Escherichia coli*).

In the case of a retroviral genetic display package, long terminal repeat sequences, a tRNA primer binding site and a polypurine tract should preferably be included to ensure reverse transcription and integration of the encapsidated RNA in an infected target cell. It may also be desirable to include a selectable marker gene in the encapsidated nucleic acid to facilitate recovery of sequences encoding the displayed polypeptide from infected target cells after a round of selection.

DNA constructs encoding virally incorporated glycoproteins have not previously been constructed according to the format outlined above, presumably because the concept of using eukaryotic viruses as replicable display packages to facilitate novel selection strategies has not previously been entertained (PCT/U.S. Ser. No. 89/03731).

Thus, viral encapsidation signal sequences were not included in the constructs used to demonstrate viral incorporation of CD4 or CD4/viral envelope chimaeric proteins into RSV or VSV particles (Young et al, 1990 Science 250 p1421–1423; Schubert et al, 1992 J Virol 66 p1579–1589) and the recombinant HSV-1 genome used to demonstrate inefficient incorporation of CD4 into HSV virions (Dolter et al, 1993 J Virol 67 p189–195) is too large (170 kbp) for convenient manipulation.

The present inventors therefore designed and constructed the plasmid pNIPenv and have demonstrated that it exhibits all of the features necessary for the generation of retroviral genetic display libraries with which to demonstrate the selection strategies outlined below. Thus, murine ecotropic retroviral packaging cells transfected with the construct were shown to shed retroviral particles which:

(a) had incorporated the fusion polypeptide encoded by the construct comprising the Moloney MLV (mouse ecotropic) envelope spike glycoprotein fused to a hapten-binding single chain antibody;

(b) bound specifically to the hapten recognised by the single chain antibody;

(c) encapsidated the nucleic acid sequences encoding the displayed fusion polypeptide;

(d) delivered the encapsidated nucleic acid to murine target cells, whereupon it was reverse transcribed, integrated and expressed;

(e) did not deliver the encapsidated nucleic acid to human target cells. Moreover, sequences encoding the nonviral polypeptide moiety of the displayed fusion polypeptide were amplified and recovered from target cells which had been infected by the retroviral genetic display packages. Murine amphotropic packaging cell lines expressing the construct were also shown to shed retroviral particles that had incorporated the fusion polypeptide, bound specifically to the hapten NIP and were infectious for mammalian cells.

In another aspect, the present invention thus provides a recombinant viral particle capable of infecting eukaryotic cells, comprising a non viral polypeptide coupled to at least part of a viral glycoprotein and displayed on the external surface of the particle; and nucleic acid encoding the non viral polypeptide and said at least part of a viral glycoprotein, the nucleic acid further comprising a packaging signal sequence.

In this aspect, the non viral polypeptide is coupled to at least part of a viral glycoprotein. The coupling may be by fusion, or may involve the two components being held together by short range covalent or noncovalent forces.

Further, it is not necessary to use the entire glycoprotein and part or parts may be removed or modified. Typically at least the cytoplasmic and transmembrane components of the glycoprotein will be present. The glycosylated regions of the glycoprotein need not be present, so that the glycoprotein in the form used may no longer be a glycoprotein. The glycoprotein may have been modified, e.g. to destroy natural binding properties, for reasons as mentioned above.

A packaging signal sequence is a nucleic acid sequence recognised by a component of the viral particle and which mediates the inclusion of the nucleic acid in the viral particle. It is also known as an encapsidation signal sequence.

Because the viral particles of this aspect include nucleic acid encoding the non viral polypeptide and said at least part of a viral glycoprotein, the particles find application as replicating vectors for gene delivery, as will be discussed further below.

The nucleic acid may also encode structural and non-structural viral proteins which when expressed in infected target cells assemble into new infectious viral particles. The new viral particles may incorporate the coupled polypeptide and viral glycoprotein. The nucleic acid of the new viral particles may encode structural and non-structural viral proteins which on infection of target cells assemble into new infectious viral particles which incorporate the coupled polypeptide and viral glycoprotein. These properties of viral particles that encapsidate nucleic encoding the coupled polypeptide and viral glycoprotein displayed at their surface, could be critical for certain therapies. For example, a major limitation of protein-based targeted cancer therapies is the inability of the protein to penetrate the tumour. Replication competent viruses could overcome this penetration barrier since they can spread from cell to adjacent cell within the tumour. For this approach it would be desirable that the progeny viral particles are largely retained within the tumour deposit and have high infectivity for tumour cells with low infectivity for normal host cells. Multivalent surface display of a tumour-specific antibody could facilitate this.

The nucleic acid of the viral particles may be engineered to contain a sequence for transcription of an RNA product, or for expression of a protein, by the infected cells. A whole range of proteins, peptides, antisense RNA transcripts and ribozyme sequences could be encoded within the virion for therapeutic effect, as illustrated by:

a) Targeted corrective gene replacement therapy for defects of genes encoding intracellular, cell surface or secreted proteins. For example targeted ex vivo or in vivo delivery of genes to correct the defect in sickle cell anaemia or thalassaemia (globin genes to bone marrow progenitor cells), alpha-1 antitrypsin deficiency (peptides to prevent intracellular accumulation of mutant (Z) alpha-1 antitrypsin), haemophilia (factor VIII or factor IX genes to hepatocytes), familial hypercholesterolaemia LDL receptor to hepatocytes).

b) Intracellular immunisation, for example targeted in vivo delivery (to CD4 expressing cells) of genes encoding proteins, antisense transcripts or ribozymes which interrupt or abort HIV life cycle following virus entry.

c) Pharmacological gene addition, for example delivery of genes encoding therapeutic antibodies, growth factors or cytokines to specific tissues in vivo.

d) Cancer therapy. Delivery of genes encoding proteins which destroy the target cell (for example, a ribosomal toxin), indirectly stimulate destruction of target cell by natural effector cells (for example, strong antigens to stimulate immune system) or convert a precursor substance to a toxic substance which destroys the target cell (for example, a prodrug-activating enzyme). Encoded proteins could also destroy bystander tumour cells (for example with secreted antitumour antibody-ribosomal toxin fusion protein), indirectly stimulate destruction of bystander tumour cells (for example cytokines to stimulate immune system or procoagulant proteins causing local vascular occlusion) or convert a precursor substance to a toxic substance which destroys bystander tumour cells (e.g. enzyme which activates prodrug to diffusible drug). Also, delivery of genes encoding antisense transcripts or ribozymes which interfere with expression of cellular genes critical for tumour persistence (for example against aberrant myc transcripts in Burkitts lymphoma or against bcr-abl transcripts in chronic myeloid leukaemia).

The expression of any of the proteins encoded by the encapsulated nucleic acid can be regulated in known manner if required.

Regulation of gene expression by inclusion of appropriate transcriptional promoter, enhancer, silencer or locus control sequences will be essential in many applications. For example, globin gene expression must be correctly regulated for effective correction of thalassaemia defects in haemoglobin production. For cancer therapy, tumour-specific gene expression (after targeted gene delivery) would enhance the overall targeting potential of the therapy. Improved specificity of gene expression in tumour cells could be achieved by use of naturally occurring, designed (modular, based on knowledge of transcription factors present in a particular tumour) or randomly mutated and selected tissue-specific, differentiation-specific, inducible and/or transformation-sensitive control sequences to regulate expression of genes encoded by the nucleic acid of the viral particles.

The viral particles of this aspect of the invention also find application in the generation of libraries of viral display packages.

Using a similar cloning strategy to that employed to generate pNIPenv, unique Sfi I and Not I restriction sites could be inserted, for example between the codons for the 6th and 7th amino acids of the mature envelope protein in a full-length infectious molecular clone of MoMLV (Shoemaker et al, 1980 Proc Natl Acad Sci USA 77 p3932–3936), without disruption of the translational reading frame. After removing the Sfi I site in the gag coding region of MoMLV (Shinnick et al, 1981 Nature 293 p543–548), the vector could then be used to generate libraries of replication-competent retroviruses displaying variegated peptides, polypeptides or glycopolypeptides.

Another aspect of the invention thus provides a DNA construct suitable for generation of a library of viral display packages, comprising a site for insertion of a sequence encoding a non viral polypeptide capable of being coupled to at least part of a glycoprotein and of being displayed on the external surface of a viral particle; and a suitable packaging signal sequence.

The term viral display package is used to mean a recombinant viral particle capable of infecting eukaryotic cells, comprising a non viral polypeptide coupled to at least pan of a glycoprotein and displayed on the external surface of the particle, and nucleic acid encoding the non viral polypeptide and said at least part of a viral glycoprotein.

The site for insertion conveniently comprises a cloning site, preferably having 2 unique non complementary restriction sites.

The glycoprotein from which said at least part of a glycoprotein is derived is conveniently a viral glycoprotein, but this is not essential and non viral or constructed glycoproteins having suitable properties can be used.

The construct may include a marker for selection of infected cells.

A logical extension of these studies is the construction of vectors of similar design for the encapsidation of nucleic acid encoding a displayed nonviral polypeptide on any virus of any family of viruses which can infect eukaryotic cells. The construction and use of similar vectors based on other virus families is particularly obvious for enveloped viruses of limited size and complexity such as Vesicular Stomatitis Virus, Influenza Virus, Semliki Forest Virus, Sindibis Virus and Sendai Virus which display oligomeric membrane spike glycoproteins. The construction and use of similar vectors derived from viruses of the Adenovirus family is also obvious since the adenovirus fibre glycoprotein has important features in common with the MoMLV envelope glycoprotein in that it is a glycosylated homotrimer (Mullis et al, 1990 J Virol 64 p5317–5323) Devaux et al, 1990 J Mol Biol 215 p567–588) which is visible by electron microscopy as a spike projecting from the surface of the virion (Ruigrok et al, 1990 J Mol Biol 215 p589–596).

We envisage the use of such viruses in which the encapsidated nucleic acid codes for a modified viral spike glycoprotein in which non viral peptides are inserted into, or substituted for surface loops of the spike glycoprotein, or in which domains of the spike glycoprotein are replaced by nonviral peptides, polypeptides or glycopolypeptides, or in which non viral peptides, polypeptides or glycopolypeptides are inserted between domains of the viral spike glycoprotein or linked to its termini. The encapsidated nucleic acid need not encode the displayed peptide, polypeptide or glycopolypeptide as a fusion with a viral spike glycoprotein, although this is preferred. We also envisage the use of viruses in which the encapsidated nucleic acid encodes an engineered derivative of a nonviral protein such as CD4 which may be efficiently incorporated into the particles and which has been engineered to display a non viral peptide, polypeptide or glycopolypeptide. We also envisage the use of viruses in which the nonviral peptide, polypeptide or glycopolypeptide is anchored in the virus particle by fusion to a synthetic transmembrane polypeptide. Also envisaged is the use of particles encapsidating nucleic acid encoding bispecific diabodies (Holliger et al, 1993 Proc Natl Acad Sci USA, 90 p6444 6448) or other "viral coat protein modifiers" as genetic display packages. The diabody would act as a "viral coat protein modifier", binding at one end to the virus and at the opposite end to the surface of a target cell. For the generation of libraries of such genetic display packages, the viral coat protein modifier should bind with high affinity to the viral particles before or during their release from the target cell, and should not be produced in excess over the viral coat proteins.

Generation of a Library of Genetic Display Packages which can Infect Eukaryotic Cells The unique noncomplementary restriction sites (Sfi I and Not I) in pNIPenv which flank the sequences encoding the nonviral polypeptide (single chain antibody) moiety of the displayed protein were chosen to facilitate the rapid cloning of any PCR-generated library of DNA fragments into this site and to facilitate the direct shuttling of DNA fragments from pre-selected phage antibody libraries incorporating the same flanking restriction sites. Clearly, there are alternative combinations of noncomplementary restriction sites which would serve equally well and in some cases (the insertion of random sequences encoding short peptides, for example) a single restriction site should should be sufficient.

The generation of a diverse library of recombinant retroviruses has been demonstrated previously by transient transfection of retroviral plasmids into retroviral packaging cells (Murphy and Efstratiadis, 1987 Proc Natl Acad Sci USA 84 p8277–8281). The library size is limited by the efficiency of plasmid transfection, first into E.coli for growth and purification of the plasmid ligation product and second into the retroviral packaging cells for generation of the retroviral genetic display library. Employing recently developed and highly efficient methods of gene delivery to mammalian cells (Curiel et al, 1992 Hum Gene Ther 3 p147–154), we estimate that a library size of $10^8$ retroviral genetic display packages should be possible.

It is proposed to use this approach to generate libraries of recombinant viruses whose members encapsidate nucleic acid sequences encoding the nonviral peptides, polypeptides or glycopolypeptides which are displayed at their surfaces. There are a number of post-translational modifications to polypeptides which occur uniquely in eukaryotic cells, are not possible in prokaryotic host cells and are required for correct folding and function of the polypeptides. The generation of libraries displaying such polypeptides (glycoproteins, for example) is therefore not possible using prokaryotic genetic display packages such as the bacteriophage display system, but is possible using eukaryotic display packages as disclosed in this invention.

Libraries can be produced of a wide range of peptides and glycopeptides, e.g. antibodies, antibody fragments such as single chain antibodies, T cell receptors, growth factors, adhesins, selectins etc.

In a further aspect the present invention thus provides a library of viral display packages prepared using the DNA construct of the invention.

Novel Selection Strategies

Variegated libraries of recombinant viruses which encapsidate nucleic acid encoding non viral peptides, polypeptides or glycopolypeptides displayed at their surface provide the basis for novel selection strategies. Previously, using phage display libraries, various selection strategies have been employed to select and isolate members of the library on the basis of the binding specificity, binding affinity, or catalytic activity of the displayed polypeptide. However, phage display libraries do not provide for methods which select for the ability of a displayed polypeptide to enhance delivery of nucleic acid into a eukaryotic target cell. Nor has the concept of such an application for a library of replicable display packages been previously disclosed.

The efficiency of delivery of nucleic acid into a target cell by a virus is influenced, by the specificity and affinity of the initial interaction between the virus and the target cell surface. The present invention therefore provides for novel methods of selection (based on the presence of the viral nucleic acid in the infected target cell) to isolate nucleic acid sequences encoding polypeptides which, when displayed on the surface of a recombinant virus, can increase the efficiency with which the virus delivers; its encapsidated nucleic acid to the interior of a eukaryotic target cell, either in a cell-specific or a non-cell-specific manner.

The fate of the nucleic acid delivered to a target cell by a virus (intracellular transport, genome conversion, integration, amplification, gene expression) is influenced by the infectious entry pathway which in turn is influenced by the specificity of the initial interaction between the virus and the target cell surface (Goud et al, 1988 Virology 163 p251–254, for example). The invention therefore provides for novel methods of selection (based on the intracellular localisation, conversion from RNA to DNA, integration, amplification or expression of the viral nucleic acid in the infected target cell) to isolate nucleic acid sequences encoding polypeptides which, when displayed on the surface of a recombinant virus, can enhance the efficiency of delivery of the encapsidated nucleic acid to the interior of a eukaryotic target cell via a non-abortive infectious entry pathway.

The fate of the nucleic acid delivered to a target cell by a virus is also influenced by host cell factors (such as the state of activation of the host cell or its position in the cell cycle) which themselves can be influenced by signalling molecules which interact with receptors on the surface of the target cell (Springett et al, 1989 J Virol 63 p3865–3869; Harel et al, 1981 Virology 110 p2b2–207). The invention therefore provides for novel methods of selection (based on the intacellular localisation, conversion from RNA to DNA, integration, amplification or expression of the viral nucleic acid in the infected target cell) to isolate nucleic acid sequences encoding polypeptides which, when displayed on the surface of a recombinant virus, can transmit a signal to the target cell which leads to alterations in the interior of the target cell that regulate the fate of the delivered nucleic acid, e.g. expression thereof.

The experimental parameters which are amenable to manipulation and which may affect the outcome of such selection procedures include:

1. The underlying composition of the viruses in the library which is in turn determined by the de sign of the vector plasmid and packaging system used to generate the library.

The nucleic acid encapsidated in the viruses may be nondefective (ie competent for the production of infectious progeny viruses in infected target cells) or defective and may or may not include selectable marker genes (conferring antibiotic resistance, for example).

The surface composition of the viruses in the library (and hence their starting host range properties) is determined initially by the choice the packaging system. For example, by appropriate choice of packaging cells, the RNA transcript and encoded fusion protein of a pNIPenv-derived library can be incorporated into retroviruses which also display unmodified mouse ecotropic MLV envelope proteins, unmodified mouse amphotropic MLV envelope proteins, or which do not display unmodified envelope proteins.

The starting host range of the viruses in the library may be further determined by the nature of the viral moieties of the modified spike glycoproteins, employed to anchor the displayed nonviral polypeptides in the viruses.

2. The composition of the library of displayed polypeptides.

This may comprise a diverse collection of peptides, antibody fragments (Fv, scFv, Fab), T-cell receptors, variants of a growth factor, cytokine, viral protein or enzyme generated by random mutagenesis, a cDNA expression library etc. The library may be derived from a larger phage display library pre-selected for a specific binding activity or catalytic activity and subcloned into the viral display vector.

The size of the library (ie diversity, number of viruses displaying a unique nonviral polypeptide) is determined by the methods used to generate diversity in the vector inserts encoding the displayed polypeptides, the efficiency of their introduction into the vector cloning site, the efficiency of the introduction of the vector into E. coli and the efficiency of introduction of the vector plasmid library into the packaging cells. There are numerous methods available to generate diversity in a library of viruses, and these have been described previously in relation to phage antibody libraries. The lox-cre, or other recombinase systems which are active in eukaryotic cells may be employed to further increase the diversity of the library by the random recombination of components of the vector inserts.

The final virus titre in the library will be a product of the diversity of the library and the number of copies of each species in the library. Titre is a function of the efficiency of the packaging system, which relates to the efficiency of expression of the vector and helper functions (ie viral structural and nonstructural proteins), and to the efficiency of amplification and encapsidation of the vector genome in the packaging cells. The virus titre could therefore be enhanced, for example, by the use of high copy number episomally replicating plasmids and/or strong cellular promoter/enhancers and by the appropriate selection of highly efficient encapsidation signal sequences.

3. Pre-adsorption of the library.

Pre-adsorption of the library of viruses by its application to a surface coated with purified antigen or by its application to nontarget cells can be used to deplete the library of viruses with unwanted binding specificities.

The choice of antigens or nontarget cells for pre-adsorption conditions selected for the pre-adsorption step (time, temperature, pH, composition of medium, presence of blocking proteins etc) may significantly influence the outcome of the selection procedure.

4. The composition of the target cells.

The species of origin, tissue of origin, state of differentiation, state of activation, state of synchrony and proliferative status of the target cells are important variables which will influence the outcome of the selection strategy.

The absolute number and purity of the eukaryotic target cells can also be varied.

There may be circumstances in which the target cells remain in their natural environment in a living organism or are artificially implanted into a living organism.

5. The conditions under which the library of viruses is contacted with the target cells.

The time, temperature, pH, composition of medium, presence of competitor antigen or blocking proteins etc may significantly influence the outcome of the selection procedure.

The target cells may alternatively be contacted with the library of virus-producing cells.

The library may be contacted with target cells in a living organism by the direct inoculation (by any route) of the vector library, the library of viruses or a library of virus-producing cells.

6. The treatment of the target cells subsequent to their exposure to the virus library.

The target cells may be maintained in tissue culture (or in a living organism) for a variable period of time without further selection.

A pure population of target cells may be selected from a mixed population of target cells, for example by fluorescent staining and fluorescence-activated cell sorting.

The target cells may be stimulated, for example by the application of selected growth factors or cytokines.

The target cells may be selected on the basis of their expression of the delivered viral nucleic acid. If the viral nucleic acid encodes an antibiotic resistance marker such as neomycin phosphotransferase, exposure of the cells to the antibiotic G418 will select for those cells expressing the viral nucleic acid. The viral nucleic acid sequences can be recovered from the infected target cell population before or after it has been subjected to a further selection process to eliminate those cells which were not successfully infected or which do not express the protein(s) encoded by the delivered nucleic acid. Alternatively, the target cell population could be stained with fluorescent antibodies against the viral component of the modified spike glycoprotein (MoMLV envelope glycoprotein, for example) encoded by the viral nucleic acid and positively staining cells could be isolated by fluorescence-activated cell sorting (FACS). FACS would also facilitate the selection of cells on the basis of the level of expression of the transferred nucleic acid. Fluorescent staining of cells for expression of the MoMLV envelope spike glycoprotein has previously been demonstrated (Chesebro et al, 198 Virology 112 p131–144).

7. The mechanism of recovery from the infected target cells of the delivered nucleic acid which encodes the displayed polypeptide.

The recovery of the nucleic acid sequences encoding the virus-displayed nonviral peptide, polypeptide or glycopolypeptide after the delivery of the nucleic acid to the a target cell can be achieved by PCR amplification using flanking oligonucleotide primers as demonstrated in example 1. PCR amplification may be from whole cells, from high molecular weight DNA or low molecular weight DNA extracted from the cells or from cDNA prepared from RNA extracted from the cells.

Alternatively, the viral nucleic acid could be amplified and recovered directly from the infected target cells into progeny viruses by superinfection with wild-type virus, by transfection of a suitable helper plasmid (encoding the retroviral gag and pol proteins if using the vectors disclosed in example 1), or by using a library of recombinant viruses encapsidating a full-length infectious viral genome inclusive of the sequences encoding the displayed polypeptide.

8. Number of rounds of selection.

After recovery of the viral nucleic acid encoding the displayed nonviral polypeptide, it may be desirable to use them to create a secondary library of viruses for further rounds of selection. This could be achieved by digesting the PCR amplification product with appropriate restriction enzymes (Sfi I and Not I if using the vectors disclosed in example 1) and cloning the digested product into the original vector. There is no limit to the possible number of rounds of selection.

9. Diversification of the product of previous rounds of selection and the generation of secondary libraries for subsequent rounds of selection.

Such diversification between successive rounds of selection provides for the directed evolution of the displayed polypeptides towards a desired biological function (Joyce, December 1992 Scientific American p48–55).

Various methods may be employed for the diversification of the nucleic acid sequences derived from a round of selection and the similar application of many such methods has been demonstrated previously using phage display libraries.

The high spontaneous mutation rates of certain RNA viruses (eg Leider et al, 1988 J. Virol. 62 p3084–3089) and their possible enhancement may also provide for novel means by which to diversify the library between rounds of selection.

Retrovirus display packages could be used for applications analagous to those which have been developed for filamentous bacteriophage. Thus, retrovirus display libraries could be selected directly on an antigen-coated solid support or indirectly with soluble biotinylated antigen followed by capture on a streptavidin-coated solid support. Bound virus could be amplified by infection of a retrovirus packaging cell line. Ecotropic virus cannot infect ecotropic packaging cells and amphotropic virus cannot infect amphotropic packaging cells due to the phenomenon of superinfection resistance. However, ecotropic virus can infect amphotropic packaging cells and vice versa. It should therefore be possible to amplify bound virus after each round of selection by infection of the appropriate (ecotropic or amphotropic) packaging cell line. The theoretical maximum achievable retrovirus display library size does not compare favourably with the theoretical maximum size of a bacteriophage display library. It is therefore unlikely that retrovirus display libraries will challenge the established applications of phase display libraries such as in vitro antibody selection and affinity maturation.

Retrovirus display libraries may facilitate selection of proteins which require post-translational modifications for full activity. Many of the proteins manufactured in mammalian cells (particularly cell surface and secreted proteins) are subject to post-translational modifications such as glycosylation or proteolytic cleavage. These post-translational modifications, which may be critical for the functional activity of the mature protein, do not occur in E.coli or other prokaryotic expression systems. There is thus a group of proteins which are not amenable to functional selection in a phage display library because of their requirement for post-translational modifications which are possible only in a mammalian cell expression system. Such proteins should be amenable to selection in a retrovirus display library.

See also WO92/01047.

Potential Applications in the Field of Therapeutic Gene Transfer

1. In parallel with advances in the safety and efficiency of technologies for the transfer of genes into human cells, either ex vivo or in vivo, an era of experimental human gene therapy has begun. Gene therapy strategies have been proposed for many human diseases, including rare heritable genetic defects of which there are more than 4000 and many common diseases including cancer, AIDS, hypertension, atheroma and diabetes (Anderson, 1992 Science 256 p808–813; Friedmann, 1992 Nature Genet 2 p93–98; Russell, 1993 Cancer J 6 p21–25). The current invention therefore has potentially important application in almost every area of human medicine.

Replication-defective viruses displaying antibodies and other nonviral peptides, polypeptides or glycopolypeptides and encapsidating genes encoding therapeutic products (eg proteins, ribozymes, antisense RNA) could be used to achieve efficient and selective delivery and expression of the encapsidated genes to target cells (which may be stem cells, differentiated cells or transformed cells of any tissue of origin), to stimulate the target cell to divide or to enter a specific programme of differentiation at the time of contact between virus and target cell, or for virus purification on a solid support coated with an antigen which binds to an altered surface component of the virus.

For example, ex vivo gene delivery to human haemopoietic stem cells (HSCs) is inefficient using amphotroic retroviral vectors, a problem which is in part due to the quiescence of the HSCs but may also reflect a low density of specific receptors for amphotropic retroviruses. Thus, a modified retrovirus could be assembled to include displayed polypeptides which, singly or in combination on the same particle, could allow the purification of the recombinant retroviral particles, bind them selectively to the HSCs, enhance the efficiency of viral entry into the HSCs and trigger division of the HSCs or otherwise enhance the efficiency of gene delivery and expression in the stem cells. The HSCs may be contacted with the recombinant viruses by direct exposure to the virus or by co-cultivation with the cells producing the recombinant retroviruses.

For the genetic modification of haemopoietic stem cells (HSCs) by direct in vivo gene transfer, the recombinant retroviruses should ideally have the following properties:

They should be easy to produce and easy to purify.

They should be capable of gaining access to their intended target cell population. The bone marrow compartment, which houses the HSCs, posesses a sinusoidal circulation and should therefore be accessible to retroviral particles delivered into the bloodstream. The retroviral particles should persist intact in the bloodstream until they are delivered to the bone marrow compartment and interact with their target cells and should therefore be resistant to complement and other potentially virolytic factors in the bloodstream or interstitial fluid. They should neither bind nor infect nontarget cells which could lead to their premature sequestration in nontarget tissues.

Having gained access to the target cells, they should selectively bind to a cell surface receptor or receptors, present on HSCs but absent from nontarget cells, and this should be followed by the fusion of the retroviral envelope with the plasma membrane of the HSC and the delivery of the retroviral core particle and its encapsidated nucleic acid into the cytoplasm of the HSC.

Since most HSCs remain quiescent for long periods of time, and since retroviral reverse transcription and proviral integration proceed inefficiently in the absence of cell division, the retrovirus should also stimulate the target cells to divide at, or shortly after, the time at which it delivers its nucleic acid to the target cell.

The provirus should integrate efficiently into a predetermined site in a host cell chromosome where it does not influence the structure or expression of the genes of the host cell by cis-acting mechanisms.

The regulatory elements contained within the retroviral provirus which control the expression of the proteins encoded by the provirus should cause those proteins to be expressed at the appropriate time and at the desired level in the HSCs or in their differentiated progeny in a lineage-specific manner.

When expressed at the desired level in the genetically modified HSCs or in their progeny, the proteins encoded by the retroviral provirus should confer a therapeutically beneficial phenotype on the cells.

The altered viral surface components of this invention which can be intelligently chosen (CD34, stem cell factor), selected from virus display libraries or evolved by repeated selection and diversification of virus display libraries could therefore be incorporated into viral particles exhibiting any or all of the other desirable features mentioned above to further improve the efficiency and selectivity of gene delivery to HSCs in vivo.

Similar considerations apply to stem cells, differentiated cells and transformed cells of any tissue of origin.

2. Replicating viruses displaying antibodies or other nonviral peptides, polypeptides or glycopolypeptides could be used for targeted virotherapy. For example a virus displaying a nonviral moiety mediating infection via the lymphoma idiotype of a B cell lymphoma (tumour-specific antigen) might spread from cell to cell through a tumour deposit without infecting normal host cells. Used in conjunction with B-cell specific regulatory elements (promoters/enhancers) incorporated into the viral nucleic acid to restrict the expression of the viral genome to cells of B-lineage, it might be possible to generate a virus highly specific for the B cell lymphoma. The viral genome could be delivered to initiate the infection by direct intratumoural or systemic inoculation of a DNA construct encoding the virus, the virus itself or the cells producing the virus. The viral surface component or components mediating selective infection of the human lymphoma cells might be selected from a virus display library, generated from a phage antibody library pre-selected on the lymhoma cells or on purified idiotypic immunoglobulin derived from the lymphoma, and might be further evolved by repeated rounds of diversification and selection.

3. The nonviral peptides, polypeptides or glycopolypeptides isolated by the novel selection strategies of this invention could be used as useful components of replication defective viral gene delivery vehicles or of replication-competent viral vectors.

They may also be useful as components of any gene delivery vehicle (eg liposome, virosome, directly conjugated to DNA, physically linked to surface of preformed virus to enhance the selectivity and efficiency of gene delivery to target cells.

They may also be used to purify and clone the cellular genes encoding the cell surface proteins to which they bind.

They may also be used as therapeutic or diagnostic protein reagents or as components of such reagents for in vivo tumour targeting, tumour imaging, immunohistochemistry etc.

Viral particles in accordance with the invention may be produced ex vivo by introducing a vector containing appropriate nucleic acid into eukaryotic cells, and culturing the cells to produce viral particles. Transduced cells are selected from non-transduced cells, and virus particles may be isolated from the culture medium. e.g. by affinity chromatography.

Viral particles in accordance with the invention may also be produced in vivo by introducing a vector containing appropriate nucleic acid into eukaryotic cells in vivo.

Direct inoculation of vector (naked, coated or encapsulated) into tumour deposits, for example, would be followed by cellular uptake and expression with subsequent production of viral particles displaying a tumour-binding fusion protein. This could be the simplest way to establish virus production in vivo for the targeted virotherapy approach to cancer and may be more efficient than direct inoculation of virus for other targeted gene therapy strategies, provided that the virus-producing cells expire naturally or can be easily destroyed after a suitable time.

The viral particles of the invention may be used to infect eukaryotic cells in vivo or ex vivo by suitable administration of the particles. Direct injection of viable or killed virus-producing cells into tumour deposits may have advantages of simplicity compared to other methods of delivery, particularly with regard to tumour deposits, where the goal is selective destruction of the target tissue.

Possible Applications of Viruses Displaying Peptides. e.g. Antibody Fragments

1. Host Range Modification

Recombinant retroviruses are used for efficient transfer of non viral genes to a variety of target cells. Amphotropic retroviruses bind to a receptor which is present on most mammalian cells and are therefore used for gene transfer to human target cells. Ecotropic retroviruses bind to a receptor which is present on murine and some other rodent cells, but is absent from human cells.

The host range of an ecotropic retrovirus might be extended in a highly specific way by display of an antibody against a cellular receptor present on a specialised subset of human cells. For example, recombinant ('ecotropic') retroviruses displaying an antibody (or growth factor or peptide) against a receptor present on human haematopoietic progenitor cells (CD34 or stem cell factor, for example) might be used for targeted gene delivery to these cells, either ex vivo by incubating unfractionated bone marrow with virus, or in vivo by intravenous delivery of virus. For in vivo delivery, other modifications to the virus particles would be necessary to reduce their sensitivity to human complement.

An antibody displayed on an amphotropic retrovirus could be used as a tissue retention signal. For example, genes can be delivered into tumour deposits by direct inoculation of retroviruses or retrovirus producer cells. Virus particles displaying an antitumour antibody might be retained more efficiently at the site of inoculation.

An antibody displayed on an amphotropic retrovirus could be used to enhance it; infectivity for a specific human target cell. For example, amphotropic retroviruses; displaying anti-CD34 antibodies might transfer their genes more efficiently to human haematopoietic progenitor cells. This effect could be mediated through preferential localisation of virus on CD34 positive cells and by slowed dissociation of virus from target cell because of the high affinity multivalent interaction between CD34 on the target cell and anti-CD34 antibody on the virus.

2. Target Cell Priming

Binding, fusion and reverse transcription of the viral genome are not dependent on target cell proliferation. However, integration of the reverse transcribed viral genome and subsequent viral gene expression do not proceed unless the target cell enters S phase some short time after it has been infected. This requirement seriously limits the efficiency of gene transfer into noncycling or slowly cycling target cell populations. Thus, ex vivo gene transfer efficiencies to haematopoietic progenitor cells have tended to be low. If the virus particles were to display antibody fragments, peptides or other ligands which could stimulate the target cells to divide at the time of virus entry, the efficiency of provirus integration in the stimulated target cells might be significantly enhanced.

3. Virus Purification and Concentration

Recombinant retroviruses are difficult to purify and to concentrate. Viruses displaying functional antibody fragments or other ligands (e.g. short peptides) can be extracted from cell culture supernatant by virtue of their ability to bind to an antigen or receptor coated solid support. It should also be possible to elute the bound virus particles without damaging their integrity and infectivity. This will facilitate purification and concentration of the recombinant viruses which will be useful for ex vivo gene delivery and essential for in vivo gene delivery.

4. Selection of Antibodies, Ligands or Peptides which Bind to Cell Surface Receptors Viruses displaying peptides e.g. antibody fragments have potential applications as display packages which encapsidate the nucleic acid sequence coding for the non viral protein displayed on the particle surface. The linkage between nucleic acid coding sequence and encoded protein or peptide provides a basis for generation of virus display libraries from which it will be possible to select antibodies or other ligands with desired binding specificities and binding kinetics. The library size will be limited by the efficiency and scale with which plasmid DNA can be transfected into retrovirus packaging cells. $10^8$ members is a suggested upper limit.

A virus display library composed of ecotropic virus particles displaying antibodies, peptides or other ligands against human cell surface determinants could be screened for ability to infect human cells. Only those particles binding to appropriate human cell surface structures should be capable of delivering their nucleic acid to the human target cells. To facilitate this type of screening it will be necessary to link the nucleic acid sequence for the displayed protein to a selectable marker gene such that both are encapsidated within the viral particle. Human cells infected by recombinant 'ecotropic' particles could then be selected for expression of the marker gene. It would then be a simple matter to isolate from these cells (by PCR for example) the gene coding for the protein which was displayed on the original infectious viral particle. This strategy would represent a new approach to the functional selection of antibodies or other ligands against cell surface receptors.

5. Evolution of New Virus Tropisms

In the strategy outlined above, the integrated provirus derived from the infecting particle is rescued by PCR. An alternative would be to introduce further rounds of amplification and selection prior to resue of the provirus. Amplification could be achieved by using (as the target for infection with the retrovirus display library) a human cell line expressing retroviral gag, pol and ecotropic env proteins. Once infected, human target cells of this nature would generate replica copies of the invading retrovirus particle for use in subsequent rounds of selection on the same cells. This would also permit rescue of antibody V genes (or other sequences fused to the retroviral envelope gene) directly from progeny virions by PCR of (reverse transcribed) viral nucleic acid. Alternatively, it might be possible to generate a library of retroviral display packages capable of autonomous replication. This could be achieved by inserting the Sfi/Not cloning site into the env gene of a wild type retroviral genome, but would be dependent on the ability of the envelope fusion protein to form stable oligomers which are displayed on the viral surface in the absence of wild type envelope protein and retain the ability to mediate the post-binding events which lead to fusion of virus envelope with target cell membrane. It is possible that oligomerisation of antibody-envelope fusion protein protomers is prevented by steric hindrance between the antibody domains of adjacent protomers. Short peptides, or even single domain proteins displayed at the same site would be less likely to hinder oligomerisation by virtue of their smaller size.

The natural (high) mutation rate of a retrovirus relates to reverse transcriptase errors, and recombinations between co-packaged viral genomes during the process of reverse transcription. In conjunction with the selection and amplification strategies outlined above, these naturally occurring mutations may allow the evolution of new virus tropisms since they will lead to alterations in the fine specificity and affinity of the antibody or ligand displayed on the surface of the virions. In this way, it might be possible, for example, to generate viruses with evolved tropisms for specific types of cancer cell and to use such viruses for cancer therapy.

6. Antigen-Selection of Retroviruses Displaying Antibodies

Besides the selection strategies outlined above, retrovirus display packages could be used for applications analagous to those which have been developed for filamentous bacteriophage. Thus, retrovirus display libraries could be selected directly on an antigen-coated solid support or indirectly with soluble biotinylated antigen followed by capture on a streptavidin-coated solid support. Bound virus could be amplified by infection of a retrovirus packaging cell line. Ecotropic virus cannot infect ecotropic packaging cells and amphototropic virus cannot infect amphotropic packaging cells due to the phenomenon of superinfection resistance. However, ecotropic virus can infect amphotropic packaging cells and vice versa. It should therefore be possible to amplify bound virus after each round of selection by infection of the appropriate (ecotropic or amphotropic) packaging cell line. The theoretical maximum achievable retrovirus display library size does not compare favourably with the theoretical maximum size of a bacteriophage display library. It is therefore unlikely that retrovirus display libraries will challenge the established applications of phage display libraries such as in vitro antibody selection and affinity maturation.

Virus display libraries may facilitate selection of proteins which require post-translational modifications for full activity. Many of the proteins manufactured in mammalian cells (particularly cell surface and secreted proteins) are subject to post-translational modifications such as glycosylation or proteolytic cleavage. These post-translational modifications, which may be critical for the functional activity of the mature protein, do not occur in *E. Coli* or other prokaryotic expression systems. There is thus a group of proteins which are not amenable to functional selection in a phage display library because of their requirement for post-translational modifications which are possible only in a mammalian cell expression system. Such proteins should be amenable to selection in a virus display library.

7. Viruses Displaying Other Polypeptides

Besides the display of functional antibody fragments on viral particles, one can envisage the display of a variety of other ligands in fusion with the viral envelope protein. Peptides, growth factors, cytokines, integrins, adhesins, selectins and T cell receptors are examples of ligands which could be displayed. Additionally, by analogy with filamentous bacteriophage, it would be possible to display functional enzymes on the surface of viral particles.

8. Viruses Displaying Multiple Non viral Polypeptides

In principle, there is no reason why two different envelope fusion proteins should not be simultaneously expressed in a packaging cell and incorporated into one viral particle. This might be useful in a number of situations. For example, it may be desirable to generate particles displaying one polypeptide to mediate binding to the target cell and another polypeptide to stimulate the target cell to divide. Alternatively, a virus particle displaying two distinct polypeptides may exhibit greater specificity for target cells expressing both of the corresponding receptors than for target cells expressing only one receptor.

9. Other Enveloped Viruses Displaying Non viral Polypeptides

The electron micrograph appearances of many enveloped viruses reveal the presence of surface structures which can best be described as 'knobs on spikes'. More detailed comparison of certain unrelated viruses suggests that these EM-visible surface structures have a number of features in common. They are frequently synthesised as a polyprotein precursor which is subjected to extensive post-translational modification during its transit to the surface of the cell in which it was synthesised. N-linked glycosylation which occurs in the endoplasmic reticulum appears to be necessary for correct folding of the polyprotein precursor and this is followed by the formation of oligomers (often trimers) which are transported into the Golgi compartment. Protomers are proteolytically cleaved in the Golgi into a membrane-anchored (transmembrane) and luminal (surface) component. This cleavage does not lead to disruption of the oligomeric structures since the surface and transmembrane components remain (covalently or noncovalently) associated, with the new hydrophobic N-terminus of the transmembrane components buried in the centre of the oligomeric structure. After additional carbohydrate processing, the oligomeric structure arrives at the cell surface, and is incorporated into budding viral particles. Studies of influenza haemagglutinin. (HA), which conforms to the pattern outlined above, indicate that docking to the target cell membrane is followed by a conformational change in the HA trimer leading to exposure of the buried hydrophobic N-termini of the transmembrane component. These exposed hydrophobic sequences are thought to initiate the fusion of virus envelope and target cell membrane by penetrating the lipid membrane of the target cell.

Figure 6:
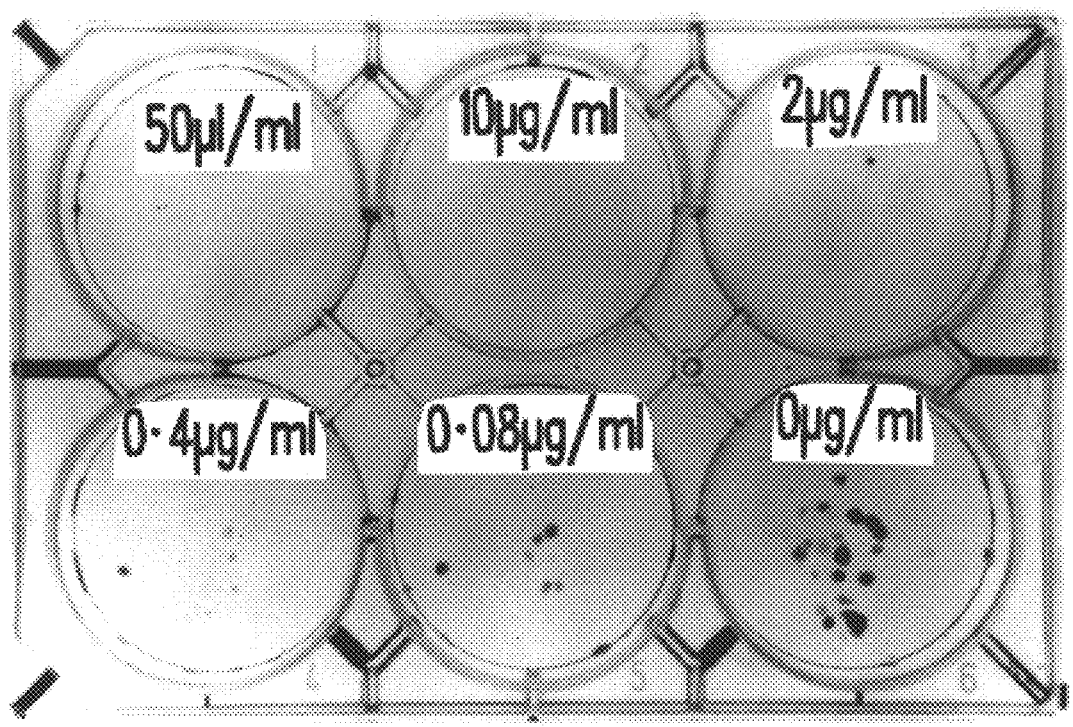

Thus, despite the lack of sequence homology between the envelope proteins of unrelated viruses, there is good reason to believe that they adopt similar three-dimensional structures and utilise similar mechanisms for docking and fusion with the target cell membrane. All mammalian viruses whose envelope proteins conform to this pattern (examples include other retroviruses, orthomyxoviruses and paramyxoviruses) should therefore be amenable for surface display of non viral polypeptides according to the strategy which we have successfully adopted for Moloney MLV. Possible advantages offered by other viruses include higher virus titres, higher mutation or recombination rates, ability to use different cell surface molecules as surrogate receptors, ease and speed of virus production, higher density and absolute number of nonviral polypeptides incorporated per virion.

10. Targeted Gene Delivery

Replication-defective viruses displaying antibodies and other non viral peptides, polypeptides or glycopolypeptides can be used for targeted gene delivery, increased efficiency of gene delivery, stimulation of cell division at time of contact between virus; and target cell, virus purification. A good example would be using human haemopoietic stem cell as a target. Ex vivo gene delivery to these cells requires that they be purified and stimulated to divide, and occurs at low efficiency with retroviral vectors (which do better than any other vector). Modified virus could include displayed polypeptides which, singly or in combination, target the stem cells (without the need for purification), trigger division of the stem cells (with no need for stimulation) or otherwise enhance the efficiency of gene delivery to stem cells. In vivo gene delivery to these cells requires efficient targeting and stimulation of division of target cell. One could deliver virus as DNA constructs, virus or as virus-producing cells.

11. Targeted Virotherapy

Replicating viruses displaying antibodies and other non viral peptides, polypeptides or glycopolypeptides can be used for targeted virotherapy. A good example would betreatment of B-cell lymphoma, using a virus which displays a non viral moiety mediating infection via the lymphoma idiotype (tumour-specific antigen). The virus would spread through the tumour deposit without infecting normal host cells. Use in conjunction with B-cell specific promoters/enhancers, should give highly specific virus. Again, one could deliver a virus as DNA construct, virus or virus-producing cells.

12. Novel Selection Strategies

Non viral peptides, polypeptides or glycopolypeptides isolated by novel selection strategies can be used:

(a) As virus components for applications outlined in 10 and 11 above.

(b) As components of any gene delivery vehicle (e.g. liposome, virosome, directly conjugated to DNA, physically linked to surface of preformed virus).

(c) As therapeutic or diagnostic protein reagents (e.g. tumour-targeting reagent).

(d) As components of such therapeutic or diagnostic reagents.

(e) As a means to clone the genes encoding the cell surface components to which they bind and subsequent use of such cell surface components.

The encoded protein could alternatively be a viral coat protein modifier such as a bispecific (anti-virus, anti-X) diabody, which associates with the virus before or immediately after it is released from the cell such that anti-X moiety is displayed on the outide of the virion.

13. Gene Therapy

Viral vectors displaying non viral proteins or peptides may also offer a vehicle for somatic gene therapy (Friedmann, 1989, Science, 244, 1275–1281). Retroviruses can transfer genes efficiently to cells but they deliver their therapeutic genes to both target and nontarget cells, necessitating local delivery of the recombinant retroviruses to specific target tissues (Nabel et al, 1990, Science, 249, 1285–1288; Ferry et al, 1991, Proc Natl Acad Sci USA, 88, 8377–8381), or retrovirus mediated gene transfer to target cells ex vivo, followed by reimplantation of these cells (Rosenberg et al., 1990, N Engl. J. Med. 323, 570–578). An alternative strategy would be to alter the host range of the virus (Russell S J (1990) Recombinant viruses expressing lymphokine genes: Their construction and use to modulate growth of transplantable rodent tumours. PhD Thesis London University) which is determined in part by the binding properties of the proteins displayed at its surface (Marsh et al, 1989, Adv Virus Res, 36, 107–151), as discussed above.

The invention will be further described by way of illustration in the following examples and with reference to the accompanying Figures, in which:

FIG. 1(*a–c*) illustrates construction of the plasmid pNIPenv; (A) describes the subcloning of the $\Psi^+$ env fragment from pCRIP; (B) describes the introduction of restriction sites into the env gene for addition of B1.8 scFV sequences; and (C) describes the addition of B1.8 scFV sequences to the subclone of (A) to generate pNIPenv.

FIG. 2 illustrates plasmids pNIPenv and pDCNeo, including sequence (SEQ ID Nos: 6 and 8) and translation(SEQ ID Nos 7 and 9) of pNIPenv expression vector showing details of fusion between MoMLVenv and B1.8 scFv. LTR=long terminal repeat; L=33 aminoacid env leader peptide: SV40E=early promoter; enh−=enhancer deletion.

FIG. 3 shows the results of supernatant ELISA for B1.8scFv-MoMLVenv fusion, protein binding to NIP.BSA.

FIG. 4 is an electron micrograph (×20,000 magnification) of NIP.BSA-agglutinated virus from psi2-NEPenv5 supernatant.

FIG. 5 is an IRISA plate (5% Giemsa). Wells were coated as indicated and bound virus was detected by transfer of G418 resistance to NIH3T3 cells. Psi2-NIPenv5-derived virus binds specifically to NIP.BSA-coated wells.

FIG. 6 is an inhibition IRISA plate (5% Giemsa). All wells were coated with NIP.BSA. Psi2-NIPenv5-derived virus (1ml) was preincubated with varying concentrations of soluble NIP.BSA, as indicated on the photograph, prior to assay. Virus binding is progressively inhibited with increasing concentrations of soluble NIP.BSA.

Figure 7:
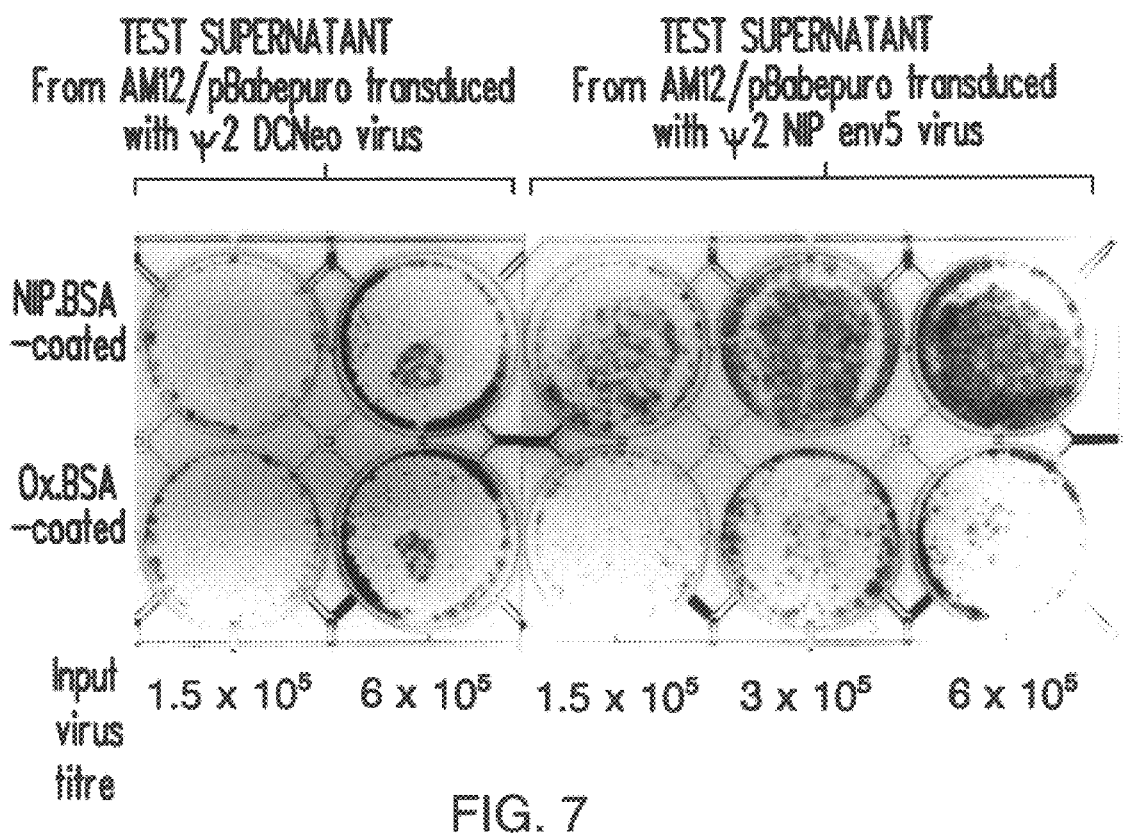

FIG. 7 is an IRISA plate (5% Giemsa). Wells were coated as indicated and bound virus was detected by transfer of puromycin resistance to NIH3T3 cells. Virus expressed by an amphotropic producer cell line infected with psi2-NIPenv5-derived virus binds specifically to NIP.BSA-coated wells.

Figure 8:

FIG. 8 illustrates recovery of integrated (proviral) B1.8 scFv coding sequences from GP+envAm12-BabePuro after infection with psi2-NIPenv5 virus by PCR amplification.

EXAMPLES

Example 1

MATERIALS AND METHODS
Plasmid Construction

The BamHI/ClaI env fragment (nt 6537–7674, nt numbering from Shinnick T M, Lerner R A, and Sutcliffe J G (1981) Nature, 293, 543–548) from pCRIP (gift from O. Danos (Danos O and Mulligan R C (1988) Proc Natl Acad Sci USA, 85, 6460–6464)) was cloned into the BamHI/ClaI backbone fragment of pZipNeoSV(X) (gift from R. Mulligan—see Cepko C L, Roberts B E and Mulligan R C (1984) Cell, 37, 1053–1062) to generate an intermediate plasmid penvBam/Cla.

Figure 1B:
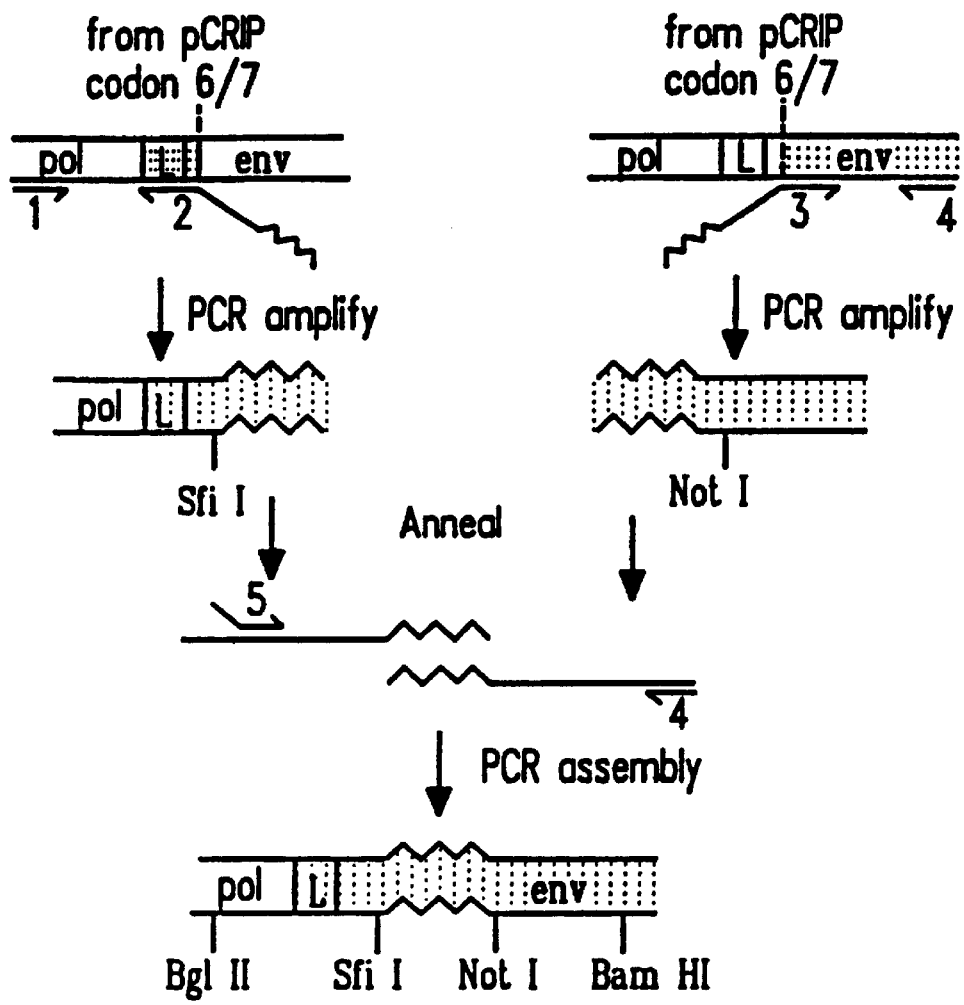
Figure 1C:
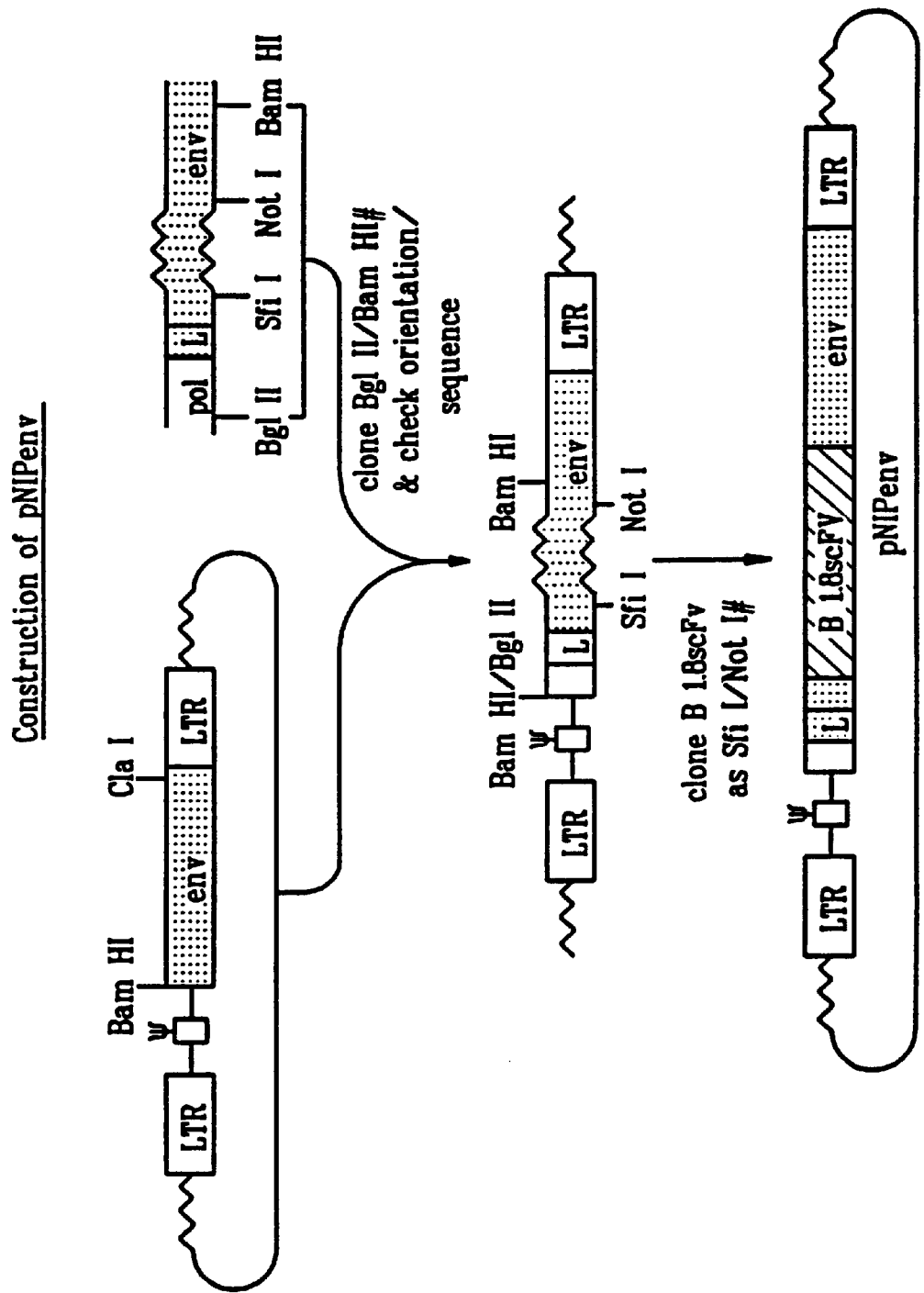

A SfiI/NotI cloning site was introduced beyond the leader peptide sequence between codons corresponding to the 6th and 7th aminoacids (from the N-terminus) in the mature MoMLV env polypeptide. The oligonucleotides envNotrev (5'-CTG CAG GAG CTC GAG ATC AAA CGG GCG GCC GCA CCT CAT CAA GTC TAT AAT ATC-3' (Seq. Id. No. 1), complementary to MoMLV env nts 5894–5914 with a 33nt 5' sequence encoding a NotI site and 21nt complementary to the 5' tail of envSfifor) and envseq (Nabel E G, Plautz G and Nabel G J (1990) Science, 249, 1285–1288) (5'-GCC AGA ACG GGG TTT GGC C-3' (Seq. Id. No. 2), complementary to MoMLV env nts 6600–6581) were used to amplify a 739bp fragment from plasmid pCRIP (and encoding downstream of codon 6). A second set of oligonucleotides, envSfifor (5'-TTT GAT CTC GAG CTC CTG CAG GGC CGG CTG GGC CGC ACT GGA GCC GGG CGA AGC AGT-3' (Seq. Id. No. 3), complementary to MoMLV env nts 5893–5873 with a 36nt 5' overhang encoding a SfiI site and 21nt complementary to the 5' tail of envNotrev) and revMLVpol (5'-AAT TAC ATT GTG CAT ACA GAC CC-3' (Seq. Id. No. 4), complementary to MoMLV pol nts 5277–5249) was used to prime amplification of a 702 bp fragment from pCRIP (and encoding upstream of env codon 7). Amplifications were carried out using Vent polymerase and reactions were subjected to 15 PCR cycles at 94° C. for 1 min, 60° C. for 1 min and 72° C. for 1 min. The 702 and 739 bp gel-purified PCR products were linked through their complementary 21nt tails to generate an env gene fragment incorporating a SfiI/NotI cloning site: the two fragments were mixed and subjected to three cycles (94° C.-1 min, 40° C.-1 min, 72° C.-2min) followed by 17 further PCR cycles (94° C.-1 min, 60° C.-1 min, 72° C.-2 after addition of ologonucleotides envseq7 and Bglenvrev (5'-TAA TCA CTA CAG ATC TAG ACT GAC ATG GCG CGT-3' (Seq. Id. No. 5), complementary to MoMLV pol nucleotides 5766 to 5785 and with the 5' tail incorporating a BglII restriction site). The product, a 905 bp fragment, was digested with BglII and BamHI and cloned into the BamHI site of penvBam/Cla (see above) giving the plasmid pSfi/Notenv. Correct assembly of this plasmid was confirmed by restriction analysis and dideoxy sequencing. A SfiI/NotI fragment from pB1.8scFv, encoding a functional B1.8 scFv antibody was then cloned into the SfiI/NotI cloning site of pSfi/Notenv to generate the plasmid pNIPenv (see FIGS. 1 and 2). Plasmid pDCNeo (FIG. 2, a gift from Dr. P Allen, Institute of Cancer Research, Fulham Road, London) is a retroviral plasmid which carries the bacterial neomycin phosphotransferase gene. It generates packagable RNA, transcripts which are encapsidated into recombinant MoMLV particles and transfer G418 resistance to infected target cells.

Figure 2:
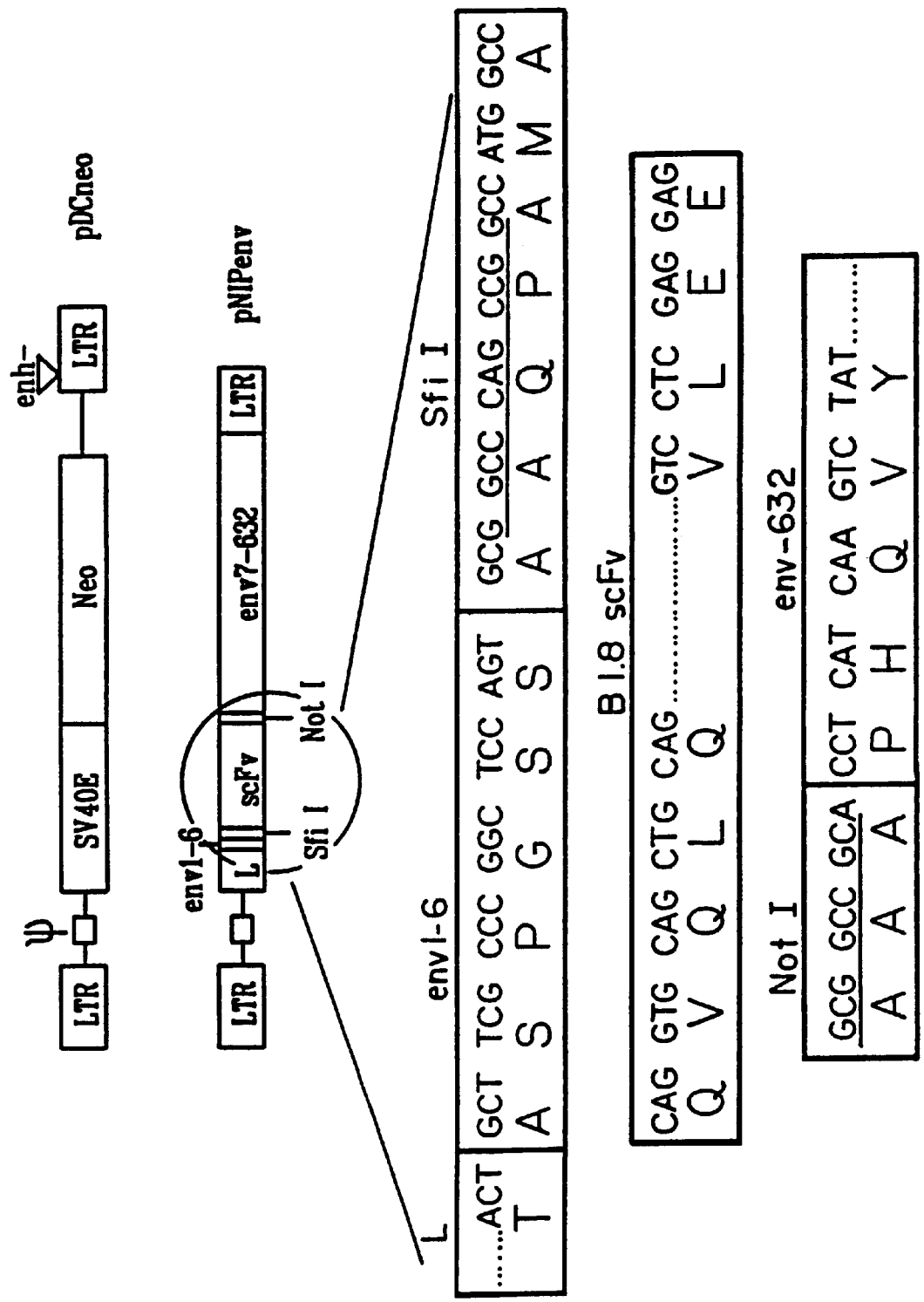

In FIG. 2, the first part of the nucleotide sequence shown is Seq. Id. No. 6, with the corresponding amino acid sequence being Seq. Id. No. 7, and the second part of the nucleotide sequence shown is Seq. Id. No. 8, with the corresponding amino acid sequence being Seq. Id. No. 9.

Cells and Recombinant Retroviruses

NIH3T3 fibroblasts, the ecotropic retroviral packaging cell line psi2 (Mann R, Mulligan R C and Baltimore D (1983) Cell, 33, 153–159) and the amphotropic retrovirus producer cell line GP+envAm12-BabePuro (a gift from RG Vile, ICRF, Lincolns Inn Fields, London—derived by transfection of GP+envAm12 (Markowitz D, Goff S and Bank A (1988) Virology, 167, 400–406) cells with the plasmid pBabePuro (Morgenstern J P and Iaand H (1990) Nucleic Acids Res., 18, 3587–3597) were maintained in DMEM/10%FBS supplemented with 60 $\mu$/ml benzylpenicillin and 100 $\mu$g/ml. streptomycin at 37° C. in an atmosphere of 5%$CO_2$. The cells were replated twice weekly using EDTA without trypsin to disrupt the monolayer.

Plasmids pNIPenv and pDCNeo were transfected (or co-transfected) into psi2 cells by calcium phosphate precipitation (Graham F L and van der Eb A J (1973) Virology, 52 456–467). Briefly, 2×10$^5$ cells were plated in 90 mm tissue culture plates (Nunc), cultured overnight, washed and fed with 10 mls new medium. 10 $\mu$l plasmid DNA and 50 $\mu$l 2M $CaCl_2$ (0.2 $\mu$m-filtered) were diluted in sterile water to a volume of 400 $\mu$l. The $CaCl_2$/DNA mi was added dropwise to an equal volume of 0.2 $\mu$mn-filtered 2×HEPES-buffered saline (280 mM NaCl, 10 mM KCl, 1.5 mM $Na_2HPO_4.2H_2O$, 12 mN dextrose, 50 mM HEPES, pH adjusted to 7.05 with 0.5N NaOH) and left to stand for 20 minutes at RT. The transfection solution (800$\mu$l) was added to the cells which were cultured for 16hrs, washed and re-fed. G418 selection (1 mg/ml) was commenced 24 hrs later and continued for approximately 2 weeks.

Transfected colonies expressing surface B1.8 single chain antibody were identified by panning with NIP.BSA-coated beads. Briefly, tosyl activated paramagnetic beads (Dynal, Oslo, Norway. Prod. no. 14004) were coated with NIP.BSA (about 10 NIP-caproate-O-succinimide molecules coupled to each bovine serum albumin molecule Hawkins R E, Russell S J and Winter G (1992) J Mol Biol., 226, 889–896), washed extensively in PBS and blocked with DMEM/10%FBS. 90 mm tissue culture plates containing up to 50 G418-resistant psi2 colonies were rocked gently for 1 hr at 4° C. followed by 1 hr at room temperature with 2×10$^7$ (50$\mu$l) beads in 5 mls DMEM/10%FBS. After 5 washes in PBS, positive colonies (heavily coated with paramagnetic beads) were easily identified and were transferred individually for further growth and harvest of cell supernatants.

Recombinant retrovirus titres were determined by transfer of G418 or puromycin resistance. NIH3T3 cells were infected by overnight exposure to 0.45 $\mu$M-filtered viral supernatants in the presence of 5 μg/ml polybrene and colonies resistant to 1 mg/ml G418 or 1.25 μg/ml puromycin were counted after 10–14 days. The amphotropic producer cell line GP+envAm12-BabePuro was infected with ecotropic virus by exposing $10^5$ cells overnight (twice) to 10 mls of the appropriate producer cell supernatant in the presence of 5 μg/ml polybrene.

ELISA for B1.8scFv-MoMLVenv Fusion Protein

To detect the B1.8-env fusion protein in supernatant of pNIPenv transfected clones. 96-well microtitre plates (Falcon) were coated overnight at RT with 20 μg/ml NIP.BS or BSA alone, blocked for 2 hrs at 37° C. in DMEM/10%FCS and washed×6 in PBS. Culture supernatants, cleared of cell debris by centrifugation at 5000 RPM for 15 min were added in triplicate to coated wells and incubated for 2 hrs at RT. Wells were washed (PBS×6). The second layer was a goat polyclonal anti-Rauscher MLV env antiserum (Microbiological Associates, Inc. Bethesda), diluted 1/500 in DMEM/10%FCS, and incubated at RT for 1 hr. After 6 washes in PBS, the third layer HRP-conjugated rabbit anti-goat antibody (Sigma) was added, the plates incubated for a further hour at RT, washed×6 in PBS and the reaction developed with ABTS (2'2'-azinobis(3-ethylbenzthiazolone)sulphonic acid). Absorbance readings were measured at 405 nm after 20 minutes.

Infectious Retrovirus Immunosorbent Assay (IRSA)

Individual wells in 6-well tissue culture plates (Corning, N.Y.) were coated overnight at 4° C. with 100 μg/ml NIP.BSA or Ox.BSA (about 14 molecules 2-phenyl-5-oxazolone coupled to each bovine serum albumin molecule, and was a gift from C.Rada), washed 3×PBS, blocked for 2 hrs at 37° C. with DMEM/10%FBS and washed 3×PBS. Virus-containing supernatant (0.45 μM-filtered) was added (2 hrs at 37° C.), wells were washed 6×PBS and $10^5$ NIH3T3 cells were added to each well in 5 mls DMEM/10%FBS containing 5 μg/ml polybrene. After 24 hrs incubation, G418 or puromycin was added, either before or after replating. 10–14 days later, viable colonies were stained with 50% methanol/5% Giemsa and counted. For inhibition IRISA, virus-containing supernatants were pre-incubated (30 mins at room temperature) with varying concentrations of NIP.BSA.

EM Analysis of Virus Agglutination 0.45 μM-filtered virus-containing supernatants were incubated overnight at 4° C. with varying concentrations of NIP.BSA. Virions were pelleted by centrifugation at 40,000 rpm for 1 hr, resuspended in 100 μl 2% phosphotungstic acid and dropped onto Formvar-coated grids which had previously been coated with a thin layer of carbon. Transmission electron micrographs were taken with a Joel JEM100CX microscope at magnifications ranging from 10,000 to 50,000.

RESULTS

Design of pNIPenv Vector

Plasmid pNIPenv (FIG. 2) encodes a chimaeric fusion protein consisting of the ecotropic MoMLV envelope polypeptide Pr80env with a single chain Fv (scFv) (Hustin J S, Levinson D, Mudgett H M, Tai M S, Novotny J, Margolies M N et al. (1988) Proc Natl Acad Sci USA, 85, 5879–5883; Bird R E, Hardman K D, Jacobsen J W, Johnson S, Kaufman B M, Lee S M et al. (1988) Science, 242, 423–426) fragment directed against the hapten 4-hydroxy-5-iodo-3-nitrophenacetyl caproate (NIP) Hawkins et al. 1992, loc cit) inserted 6 amninoacids from the N-terminus of Pr80env. The scFv fragment is flanked by Sfil and NotI sites as in the vector pHEN1 (Hoogenboom H R, Griffiths A D, Johnson K S, Chiswell D J, Hudson P and Winter G (1991) Nucleic Acids Res., 19, 4133–4137), to facilitate the cloning of scFv fragments selected from phage display libraries (Marks J D, Hoogenboom H R, Bonnert T P, McCafferty J, Griffiths A D and Winter G (1991) J Mol Biol, 222, 581–597). The 33 aminoacid MoMLV env leader sequence is retained, without disruption of the leader cleavage site. The N- and C-termini of the B 1.8scFv are connected to adjacent env sequences through short linker sequences (FIG. 2). Expression is driven from promoter/enhancer sequences in the 5' MoMLV long terminal repeat (LTR) and a polyadenylation sequence is provided by the 3' MoMLV LTR.

Display of Antibody Fragments on Surface of Mammalian Cells

Plasmid pNIPenv was co-transfected with the retroviral plasmid pDCNeo (which generates a packagable RNA transcript encoding neomycin phosphotransferase and confers G418-resistance, FIG. 2) into the ecotropic retroviral packaging cell line psi2. Control cells were transfected with pDCNeo alone. G418-resistant psi2 transfectants displaying the B1.8 scFv-MoMLVenv fusion protein at their surface were identified by panning with NIP.BSA-coated paramagnetic beads. The cells isolated by panning were heavily coated with the beads, indicating that a functional antibody fragment was displayed on the surface of the transfected cells.

Display of Antibody Fragments on Surface of Retrovirus

Figure 3:
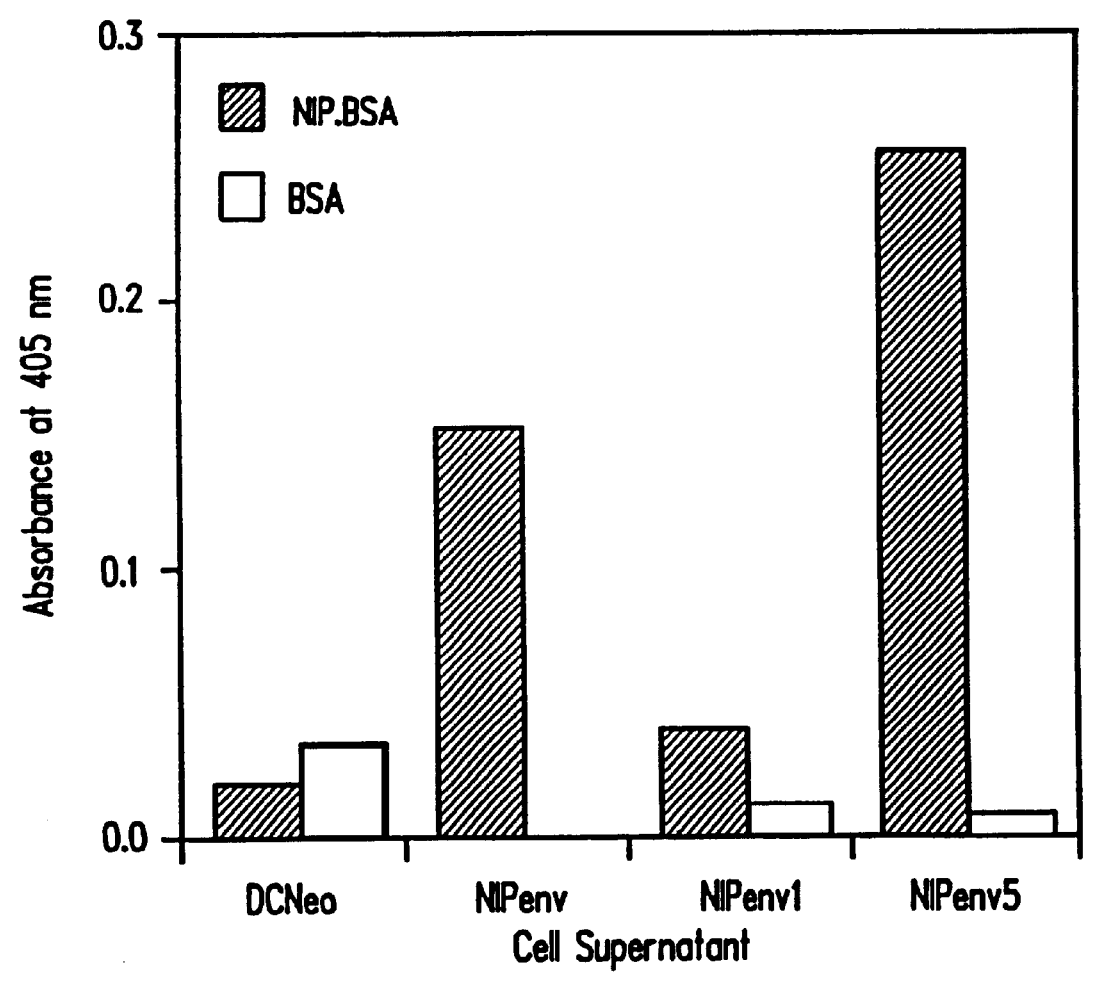

The retroviruses expressed from the selected clones were titred by transfer of G418 resistance to NIH3T3, and a range of titres noted, for example clones psi2-NIPenv1 (titre 0 G418 t.u./ml) and psi2-NIPenv5 (titre $10^3$ G418 t.u./ml). Cell supernatants were then tested by ELISA for presence of the B 1.8scFv-env fusion protein (FIG. 3). Using anti-env antiserum as the second layer, specific NIP.BSA-binding activity was detected in supernatants from pooled pNIPenv psi2 clones (titre 103 G418 t.u./ml) and from clone psi2-NIPenv5, but not from clone psi2-NiPenv1 or pooled psi2-DCNeo clones (titre $10^3$ G418 t.u./ml). This suggested that the functional antibody fragment could be incorporated into virion particles and displayed at their surface.

Figure 4:
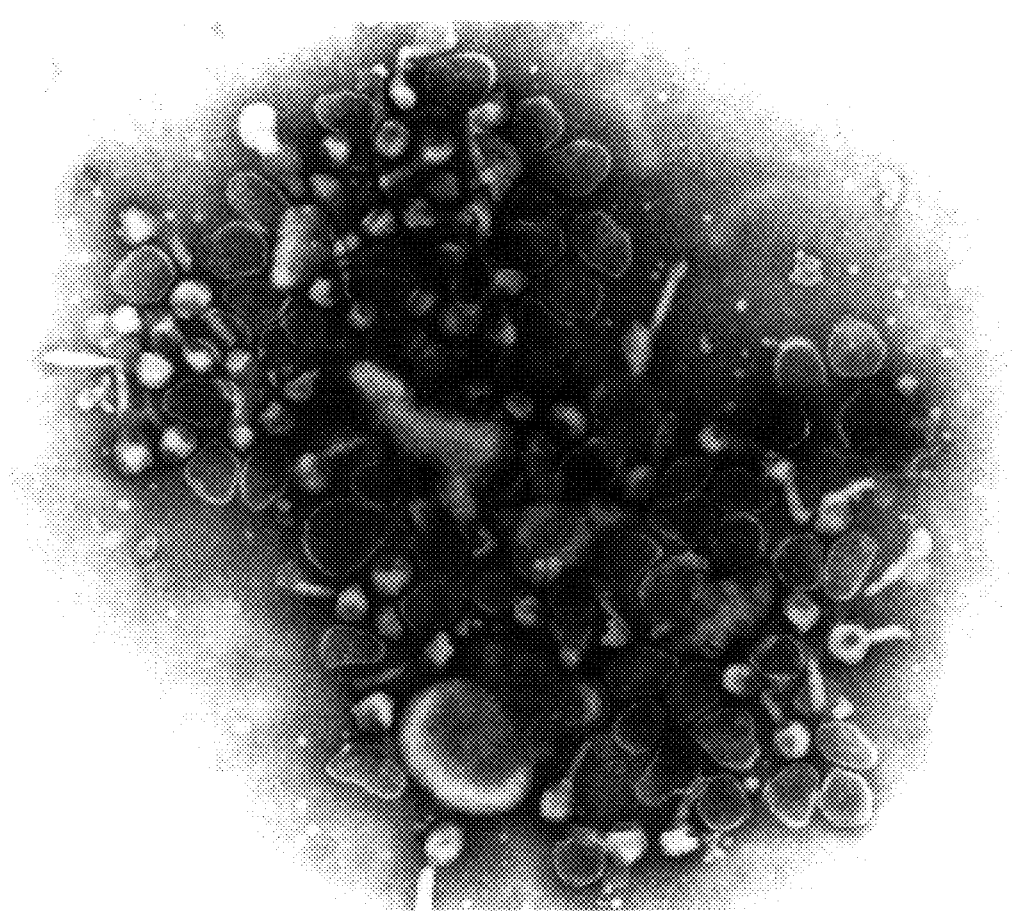

As a further demonstration, 0.45 μM-filtered culture supernatant psi2-NIPenvS-virus was incubated with varying concentrations (0, 0.1, 1.0 and 10.0 μg/ml) of NIP.BSA and the resuspended viral pellet examined by electron microscopy for virus agglutination. At 10 μg/ml NIP.BSA, numerous large aggregates of MoMLV particles with typical morphology (Dalton A J, Haguenau F and Moloney J B (1964) J Natl Cancer Inst., 3,3 255–275) were observed (FIG. 4). Individual virions were closely apposed with, a relatively uniform interparticle distance (6–20 nm), indicating crosslinking by NIP.BS A. Similar aggregation was not observed in the absence of NIP.BSA, nor with control psi2-DCNeo supernatant.

Retrovirus Particles Displaying Antibody Fragments can Package Marker Genes

As proof that the functional antibody fragment was displayed on infectious retroviral particles, the novel IRISA assay was developed (Materials and Methods). Filtered recombinant psi2-NIPenv5 virus was bound to NIP.BSA-coated plates, washed and NIH3T3 cells added to each well. The bound virus gave rise to G418 resistant colonies (FIG. 5 and Table 1), and the binding of the virus could be competively inhibited by soluble NIP.BSA (FIG. 6). The virus did not bind to phOx-BSA-coated or uncoated tissue culture wells, nor did psi2-DCNeo virus bind to NIP.BSA. This indicates that the virus particles bind specifically to hapten, are infectious and can package a marker gene for transfer into mouse fibroblasts.

Retroviral Particles Displaying Antibody Fragments can Package the Antibody V-genes The amphotropic producer cell line GP+envAm12-BabePuro was infected with recombinant psi2-NIPenv5 virus and transfer of the hybrid B1.8scFv-MoMLV cenv fusion gene was confirmed by PCR analysis of high molecular weight DNA extracted from these cells. Results are shown in FIG. 8. High molecular weight DNA was extracted from the infected cells and amplified using PCR primers VH1BACK (Orlandi et al., 1989 Proc Natl Acad Sci USA 86 p3833–3837) and envseq5 (5'-GTA AGG TCA GGC CAC CAG GT-3' (Seq. Id. No. 10)), reverse complement of MoMLV env nucleotides 5981–5600. Amplification was carried out using Promega Taq polymerase and reactions were subjected to 30 cycles at 94° C. for 1 min, 55° C. for 1 min and 72° C. for 1 min. In FIG. 8, Lane 1=PhiX174 Hae III digest (fragment sizes 1353, 1078, 972, 603, 310, 281, 271, 234, 194, 118, 72). Lane 2=GP+envAm12-BabePuro infected with 10 mls psi2-NIPenv5 virus. Lane 3 =Uninfected GP+envAm12-BabePuro. As a demonstration of functional expression of the transferred env fusion gene, the virus particles expressed by these cells bound more efficiently to NIP.BSA coated plates than to phOx.BSA-coated plates as indicated by subsequent transfer of puromycin resistance to NIH3T3 cells (FIG. 7). In contrast, GP+envAm12-Babepuro cells infected with Psi2-DCNeo virus gave no signal when analysed by PCR for the env fusion gene and expressed virus which did not bind specifically to NIP.BSA. This indicates that psi2-NIPenv5-derived virus particles encapsidate and transfer a functional gene encoding the functional B1.8scFv antibody fragment displayed on their surface.

DISCUSSION

We have shown that a functional antibody fragment can be displayed on the surface of a retroviral particle fused to its envelope protein, and that this confers novel binding specificity on the particle. Pr85env, the initial translation product of the env gene forms oligomers, undergoes glycosylation and is proteolytically cleaved during its transport through the endoplasmic reticulum and Golgi apparatus to the cell surface where it appears as a small transmembrane C-terminal domain p15(E)TM, linked noncovalently or by a disulphide bridge to a larger extracellular domain gp70SU (Weiss R, N Teich, H Varmus and J Coffin (eds). (1985) RNA tumour viruses, volume 2. Cold Spring Harbor Laboratory, Cold Spring Harbor, N.Y.). Here we fused the scFv fragment close to the N-terminus of gp70SU and we envisage that it is folded and displayed as a, separate domain. This choice of fusion site may be important, as an attempt to replace. the N-terminal domain of gp70SU with a functional 112 polypeptide did not succeed (Russell S J (1990) Recombinant viruses expressing lymphokine genes: Their construction and use to modulate growth of transplantable rodent tumours, PhD Thesis, London University). Presumably it will prove possible to incorporate antibody fragments with different binding specificities, and indeed the restriction sites of pNIPenv were designed to facilitate the cloning of other scFv cassettes from filamentous; phage vectors (Marks et al., 1991, loc cit). It may also be possible to display other functional nonviral polypeptides (growth factors, cytokines or T cell receptors for example) or short peptide sequences with a variety of receptor binding activities.

We showed that the virus particles that display antibody fragments could also encapsidate the genes of a marker (neo), and were infectious as shown by the-transfer of G418 antibiotic resistance to murine cells from viral particles immobilised on NIP-BSA coated plates. The infectivity of these particles was expected since they incorporate both the antibody-envelope fusion protein and unmodified envelope protein which is also expressed abundantly in the retroviral packaging cell line. In principle such particles could be used for targeted delivery of a genetic marker to cells (see below). It is not known whether retrovirus can be assembled in which all the subunits of the viral envelope protein are fused to antibody, and if so whether the virus would infect cells.

We also demonstrated that virus particles displaying antibody fragments can encapsidate the genes (pNIPenv) encoding the antibody fragments on their surface and hence have potential as replicable display packages, as with phage antibodies (McCafferty et al., 1990, loc cit). (These virions could also have been selected directly by including a selectable marker gene on the pNIPenv plasmid). We suggest that it might be possible to evolve new viral tropisms (see below) using repertoires of antibody fragments or peptide sequences displayed on the virus, with cycles of infection and selection.

Retroviral particles displaying antibodies against cell surface antigens should bird preferentially to target cells expressing those antigens, and this may facilitate their infection. For some antigens, the binding of retrovirus-associated antibody fragments to cell surfaces is followed by membrane fusion between virus and target cell: streptavidin-linked biotinylated monoclonal antibodies have been used to link ecotropic retroviruses to the surface of nonpermissive human cells with subsequent transfer of the viral genome into the target cells (Roux P, Jeanteur P and Piechaczyk M (1989) Proc Natl Acad Sci USA, 86, 9079–9083). This "molecular bridging" approach was successful (but inefficient) when viral particles were coupled to human MHC class I and class II antigens, but not to the human transferrin receptor (Gould B, Legrain P and Buttin G (1988) Virology, 163, 251–254), and suggests that only a limited number of cell surface antigens can function as surrogate receptors for MoMLV particles. In an attempt to identify suitable surrogate receptors, we are currently generating ecotropic retroviral particles displaying antibody fragments against a number of target antigens present on human cells. NIP-derivatised human cells were tested as a model for targeted gene delivery, but became permissive for both modified (displaying an anti-NIP antibody) and unmodified ecotropic viral particles.

Retroviruses displaying antibody fragments might also be used to retain the retrovirus in the vicinity of a tumour, and thereby reduce the systemic spread of recombinant retroviruses. For example, it has been proposed to deliver genes encoding prodrug-activating enzymes to tumours by injection of retroviral vector-producer cells (Culver K W, Ram Z, Wallbridge S, Ishii H, Oldfield E H and Blaise R M (1992) Science. 256, 1550–1552; Stone R (1992) Science, 256, 1513), and then to administer the appropriate prodrug to kill gene-transduced tumour cells and their untransduced neighbours. As a safety measure, the retroviral particles could be engineered to display antibody fragments directed against an antigen on the tumour cells to enhance their retention within the tumour deposit.

Example 2
Host Range Modification Example

A431 is a human cell line expressing abundant EGF receptors and the monoclonal antibody 425 binds specifically to human EGF receptors. A pHen-1 derived plasmid encoding the 425 antibody as a functional, EGF receptor-binding single chain Fv was obtained from Detlef Gussow (MRC Collaborative Centre). The 425 scFv gene was cloned as a SfiI–NotI fragment into pNIPenv in place of the B1.8 scFv. The resulting plasmid (pEGFRenv) was contransfected with plasmid pBabePuro into ecotropic retrovirus packaging cells. Colonies resistant to 1.25µ per ml puromycin were either pooled or expanded individually and supernatant derived from these cells was passed through a 0.45 µM filter and tested for its ability to transfer puromycin resistance to human A431 cells. A431 cells were infected by overnight exposure to virus-containing supernatant in the presence of polybrene (8 µg/ml) and were selected for 21 days in, 0.6 µg/ml puromycin. Supernatants derived from ecotropic producer cells transfected with pEGFRenv repeatedly gave low efficiency transfer of puromycin resistance to A431 cells (approximately one puromycin resistant colony per ml of supernatant). Control virus derived from the same ecotropic packaging cells transfected with pBabePuro alone did not transfer puromycin resistance to A431 cells. We conclude from these results that retrovirus particles displaying an anti-human EGF receptor antibody fragment in fusion with the viral envelope protein have an extension to their host range and are able to infect otherwise nonpermissive cells which express the human EGF receptor.

Example 3
Possible Examples of Novel Selection Strategies

1. This example teaches how to select for a nonviral polypeptide which, when displayed on a recombinant virus, increases the efficiency with which the recombinant virus delivers the viral nucleic acid to a human target cell through a target cell-selective entry pathway which leads to the expression of the viral nucleic acid.

In this example, the experimental conditions are set such that the viruses contained in the library display no viral surface proteins capable of efficient binding to the target cells. The specific interaction of viruses in the library with the surface of the target cells and the subsequent delivery of the viral nucleic acid is therefore possible only if mediated by the virus-displayed nonviral polypeptide.

Single-chain antibodies are pre-selected from a large ($10^{10}$ diversity) random combinatorial phage antibody library for binding to the surface of the cell line K422 (Dyer et al, 1990 Blood 75 p709–714) and are subcloned as Sfi I—Not I fragments into the vector pNIPenv.

The vector plasmid library is introduced by lipofection into the psi-2 packaging cell line (Mann et al, 1983 Cell 33 p153–159) and library of recombinant retroviruses is harvested in the form of cell culture supernatant after 72 hrs. The estimated library diversity is $10^4$ members and the estimated virus titre is $10^5$ infectious particles per ml of culture supernatant. The unmodified spike glycoproteins displayed by the viruses and the viral moieties of the modified spike glycoproteins (which are fused to single chain antibody domains) are both mouse ecotropic MoMLV envelope proteins which do not bind to human cells unless they have been genetically modified to express the gene encoding the ecotropic retrovirus receptor (Albritton et al, 1989 Cell 57 p659–666; Albritton et al, 1993 J Virol 67 p2091–2096).

The retrovirus display library is pre-adsorbed on the human myeloma cell line Karpas 620 (Nacheva et al, 1990 Brit J Haem 74 p70–76) which is of B cell origin and derives from a patient with plasma cell leukaemia. $10^7$ Karpas 620 cells are added to 10 ml; of 0.2 $\mu$m-filtered virus library-containing supernatant (RPMI/10% FCS plus antibiotics) with 8 $\mu$g per ml polybrene 4° C. for 4 hours for virus preadsorption.

The pre-adsorbed virus library is then separated from the Karpas 620 cells by centrifugation and mixed with $10^6$ K422 cells (Dyer et al, 1990 Blood 3 p709–714) at 4° C. for 2 hours to allow virus binding, moving to 37° C./5% $CO_2$ for virus entry. K422 is a human B-cell line derived from a patient with follicular B-cell non-Hodgkin's lymphoma.

The viruses display only murine ecotropic virus spike glycoproteins (which do not bind human target cells) and modified murine ecotropic virus spike glycoproteins fused to single-chain Fvs pre-selected for binding to the B-cell line K422 which has the immunophenotype of a follicle centre cell. They will not deliver their encapsidated nucleic acid to the human K422 target cells unless they display a single chain Fv which can interact with a suitable receptor site on these cells which is not present on the plasma cell line Karpas 620.

The retrovirus display library is pre-adsorbed on a human plasma cell line, also of B cell lineage but more differentiated than the follicle centre cell. Viruses which remain after preadsorption are likely to be capable of infecting the K422 cells only through binding to the K422 idiotypic surface immunoglobulin (a unique tumour-specific antigen) or to differentiation antigens present on the K422 cells, but lacking on the plasma cells. Such differentiation antigens are likely to be specific to the B-cell lineage.

The infected K422 cells are refed and expanded in tissue culture for 7 days, stained with mouse monoclonal antibodies or goat polyclonal antisera against the MoMLV envelope spike glycoprotein, with second-layer fluorescent anti-mouse Fc or anti-goat Fc antibodies and positively staining cells are isolated by FACS sorting.

The viral sequences coding for a displayed single chain Fv which binds to the K422 cells, leading to viral delivery of the nucleic acid are recovered by PCR amplification from chromosomal DNA extracted from the (selected or unselected) cells, using the PCR primers BglenvRev and envseq5. The PCR product is digested with Sfi I and Not I, purified on an agarose gel and recloned in the Sfi I—Not I—digested pNIPenv backbone to generate a secondary vector library which is used to generate a secondary retrovirus display library by transfection into the psi-2 packaging cell line. The secondary retrovirus display library is subjected to a second round of the same selection procedure and the nucleic acid sequences coding for the selected single chain Fvs are recovered as previously.

At this stage the PCR product may be diversified according to a variety of previously demonstrated strategies, recloned into pNIPenv and used to generate further retrovirus display libraries for use in further rounds of selection. Thus the invention provides for methods to evolve a polypeptide which is displayed on its surface using repeated rounds of diversification and selection.

At any stage after the first round of selection, individual selected single chain antibody sequences can be isolated, subjected to sequence analysis, cloned into expression vectors and used to produce soluble antibody fragments or cloned into pNIPenv and used to produce a pure population of retroviruses displaying a single nonviral polypeptide. The purified antibody fragments and recombinant viruses can then be used to determine the identity and tissue distribution of the target antigen to which the selected single chain Fv binds.

The choice of nontarget cells (or cloned antigens) for the preadsorption step can be varied to suit the precise goals of the selection procedure. Thus, pre-adsorption on a B-cell line derived from another patient with follicular NHL, an early B-lineage cell line, the cloned K422 idiotypic immunoglobulin, a non-B cell line or a combination of different cell lines or cell lines and antigens could be used to skew the selection.

The invention therefore provides for methods to select single chain antibodies or other peptides, polypeptides or glycopolypeptides which may be used to target virus-mediated gene delivery using nonreplicating or replicating recombinant viruses to tumour cells, stem cells, or more differentiated cells from any human tissue. Targeting efficiency could be further increased by incorporating tissue-specific or tumour-selective promoters, enhancers, silencers or locus-control sequences into such recombinant viruses. The selected peptides, polypeptides or glycopolypeptides could also be used to target gene delivery by nonviral gene delivery vehicles, for example by conjugation to plasmid DNA or by incorporation into cationic liposomes. They may also be useful as components of diagnostic kits or as tools to clone cellular receptors or as components, of protein-based therapeutic reagents for targeted therapy of a variety of diseases including cancer, autoimmunity and AIDS.

2. The experimental conditions may also be set such that the viruses from which the library is derived are infectious for the target cells but increased efficiency of infection desired. Viruses in the display library are selected according to the efficiency with which they deliver the nucleic acid to the target cells. Murine amphotropic retroviral vectors, for example commonly give 10-fold reduced titre on human compared to murine cells and it is desirable to select for displayed polypeptides which overcome this deficiency. In this case, negative selection on human nontarget cells is not possible. Multiple rounds of selection and amplification are therefore required to enrich the library with members which infect the target cells most efficiently. For example, using a murine amphotropic retroviral packaging cell and the pNIPenv vector, it is possible to generate a library of viruses displaying single chain antibodies pre-selected (on phage) for binding to a T-cell line such as Jurkat and then to complete multiple rounds of selection for members of the library which infect the line most efficiently. To avoid the labour of repeatedly recloning isolated PCR fragments and retransfecting the packaging cells, it is possible to employ Jurkat cell targets stably transfected with plasmids encoding retroviral gag, pol and, xenotropic or amphotropic env proteins such that they encapsidate the delivered retroviral nucleic acid into new retroviruses for subsequent rounds of selection (alternating the xenotropic and amphotropic rescue) Diversification of the library between rounds of selection provides for directed evolution of the displayed polypeptides.

3. The selection conditions may also be set such that the viruses from which the library is derived are capable of binding to the target cells but the target cells are not dividing and can be stimulated to divide by exposure to a very low concentration of a (known or unknown) growth factor. Where the growth factor is known, the initial library of viruses may display a diverse population of artificially generated genetic variants of the growth factor. Where the growth factor is poorly defined, the initial library of displayed nonviral polypeptides may be derived from a cDNA library obtained from a cell line known to produce the factor. Following exposure to a library of retroviruses the cells are selected for expression of a marker gene delivered by the retroviral nucleic acid, a phenotype which indicates that reverse transcription and integration of the retroviral nucleic acid has occurred and that the target cell has therefore undergone cell division. Alternatively, the integrated proviral sequences can be recovered directly by PCR amplification from the high molecular weight chromosomal DNA of the target cells. The method can be used to isolate a nonviral polypeptide which triggers division of target cell in the context of viral particle. Again, diversification between rounds of selection provides for directed evolution of selected members of the original library.

4. In order to evolve a new virus tropism, the experimental conditions are set such that the viruses contained in the library are replication-competent and display no viral surface proteins capable of efficient binding to the target cells. The specific interaction of viruses in the library with the surface of the target cells and the subsequent delivery of the viral nucleic acid is therefore possible only if mediated by the virus-displayed nonviral polypeptide. Using a full-length infectious molecular clone of MoMLV, for example which includes Sfi I and Not I restriction sites as in pNIPenv, a variegated library of constructs encoding infectious (mouse ecotropic) virions which display different nonviral peptides/polypeptides/glycopolypeptides is generated. The library is applied to the human target cells with negative selection (pre-adsorption) steps on carefully chosen human nontarget cells and virus progeny are harvested after 48 hours and subjected to repeated rounds of the same selection procedure.

TABLE 1

Pooled IRISA data for psi2-NIPenv5- and psi2-DCNeo-derived virus binding to NIP.BSA or OX.BSA. Numbers represent Giemsa-stained G418 resistant colony counts (halved for assays which were replated after 24 hrs).

| | Input | NIP.BSA | Ox.BSA |
|---|---|---|---|
| | NIPenv5 | | |
| | 1950 | 14 | 2 |
| | 1950 | 20 | 1 |
| | 900 | 31 | 0 |
| | 1560 | 100 | 12* |
| | 1560 | 80 | 11* |
| | 4650 | 125 | 1 |
| | 5950 | 150 | 2 |
| Totals | 18520 | 520 | 29 |
| | DCNeo | | |
| | 1100 | 9 | 7* |
| | 625 | 0 | 0 |
| | 625 | 0 | 0 |
| | 1375 | 2 | 4 |
| Totals | 3725 | 11 | 11 |

*polybrene added to initial virus binding reaction

What is claimed is:

1. A recombinant retroviral particle that infects a eukaryotic cell, comprising (a) a fusion protein comprising a non-viral polypeptide fused to a substantially intact viral glycoprotein, wherein the substantially intact viral glycoprotein retains fusogenic activity, said non-viral polypeptide being displayed on the external surface of the particle; and (b) a nucleic acid encoding said fusion protein, the nucleic acid further comprising a packaging signal sequence.

2. A recombinant retroviral particle that infects a eukaryotic cell, said particle comprising a fusion protein comprising a non-viral polypeptide fused to a substantially intact viral glycoprotein, wherein the viral glycoprotein of the fusion protein retains fusogenic activity and the non-viral polypeptide is displayed on the external surface of the particle.

3. The particle of claim 1 or 2, wherein said recombinant retroviral particle binds specifically to a cognate receptor recognized by the non-viral polypeptide, encapsidates a nucleic acid sequences encoding the displayed fusion protein, delivers the encapsidated nucleic acid to an appropriate target cell whereupon said nucleic acid sequence is reverse transcribed, integrated and expressed.

4. The particle of claim 1 or 2, wherein the viral glycoprotein comprises a spike glycoprotein.

5. The particle of claim 1 or 2, wherein the non-viral polypeptide binds to a cell surface molecule of target eukaryotic cells.

6. The particle of claim 1 or 2, wherein the non-viral polypeptide comprises an antibody or antibody fragment.

7. The particle of claim 1 or 2, further comprising one or more viral coat proteins.

8. The particle of claim 1 or 2, wherein said particle infects human cells.

9. A library of retroviral display packages comprising a plurality of said recombinant retroviral particle of claim 2 or 3.

10. A method of identifying a nucleic acid of a retroviral display package in the library of retroviral display packages of claim 9 which is delivered into a eukaryotic cell by the package, comprising contacting packages from the library with target cells, and isolating delivered nucleic acid from the target cells, such that said nucleic acid is identified.

11. A method of identifying a nucleic acid of a retroviral display package in the library of retroviral display packages of claim 9 which is delivered into a eukaryotic cell by the package, comprising contacting packages from the library with target cells, and detecting proviral DNA in the target cells, such that said nucleic acid is identified.

12. A method of identifying a nucleic acid of a retroviral display package in the library of retroviral display packages of claim 9 which is delivered into a eukaryotic cell by the package, comprising contacting packages from the library with target cells, and detecting integrated proviral DNA in the target cells, such that said nucleic acid is identified.

13. A method of identifying a nucleic acid of a retroviral display package in the library of retroviral display packages of claim 9 which is delivered into a eukaryotic cell by the package, comprising contacting packages from the library with target cells, isolating target cells that express a delivered nucleic acid, and amplifying proviral DNA contained in said isolated target cells, such that said nucleic acid is identified.

14. A method of identifying a nucleic acid of a retroviral display package in the library of retroviral display packages of claim 9 which is delivered into a eukaryotic cell by the package, comprising contacting packages from the library with quiescent target cells, and detecting target cells undergoing mitosis, such that said nucleic acid is identified.

15. The method of claim 10, wherein the viral glycoprotein comprises a spike glycoprotein.

16. The method of claim 10, wherein said particle infects human cells.

17. The method of any one of claims 10, 12, 13 and 14, wherein said isolating, said detecting or said amplifying steps comprise PCR amplification of said delivered nucleic acid or said proviral DNA.

18. The method of any one of claims 10, 12, 13 and 14 wherein said delivered nucleic acid or said proviral DNA encodes a detectable product, and said isolating, said detecting or said amplifying steps comprises detecting said product.

19. A DNA construct suitable for generation of a library of retroviral display packages, comprising a nucleotide sequence encoding a substantially intact viral glycoprotein containing a site for insertion of a sequence from a library of sequences encoding non-viral polypeptides that permits in-frame fusion of the non-viral polypeptide to said viral glycoprotein to form a fusion protein that is displayed on the external surface of a viral particle; and a suitable packaging signal sequence, wherein said site for insertion in said substantially intact viral glycoprotein permits said viral glycoprotein to retain fusogenic activity.

20. The DNA construct of claim 19 wherein a member of said library of retroviral display packages binds specifically to a cognate receptor recognized by the non-viral polypeptide.

21. The construct of claim 19, wherein the site for insertion comprises a cloning site.

22. The construct of claim 19, comprising in the 5' to 3' direction: a 5' LTR a packaging signal sequence, a leader sequence, an Sfi I recognition site, a NotI recognition site, a sequence encoding a substantially intact retroviral envelope glycoprotein, and a 3' LTR.

23. The construct of claim 21, said site for insertion including two unique non-complementary restriction sites.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
       (A) LENGTH: 54 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 1:

CTGCAGGAGC TCGAGATCAA ACGGGCGGCC GCACCTCATC AAGTCTATAA TATC        54

(2) INFORMATION FOR SEQ ID NO: 2:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 2:

GCCAGAACGG GGTTTGGCC                                              19

(2) INFORMATION FOR SEQ ID NO: 3:

(i) SEQUENCE CHARACTERISTICS:
       (A) LENGTH: 57 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 3:

TTTGATCTCG AGCTCCTGCA GGGCCGGCTG GGCCGCACTG GAGCCGGGCG AAGCAGT     57

(2) INFORMATION FOR SEQ ID NO: 4:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 4:

AATTACATTG TGCATACAGA CCC                                                    23

(2) INFORMATION FOR SEQ ID NO: 5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 5:

TAATCACTAC AGATCTAGAC TGACATGGCG CGT                                          33

(2) INFORMATION FOR SEQ ID NO: 6:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 6:

ACTGCTTCGC CCGGCTCCAG TGCGGCCCAG CCGGCCATGG CCCAGGTGCA GCTGCAG               57

(2) INFORMATION FOR SEQ ID NO: 7:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iii) ANTI-SENSE: NO (v) FRAGMENT TYPE: internal (xi) SEQUENCE DESCRIPTION: SEQ ID NO: 7:

Thr Ala Ser Pro Gly Ser Ser Ala Ala Gln Pro Ala Met Ala
1               5                   10

Gln Val Gln Leu Gln
15

(2) INFORMATION FOR SEQ ID NO: 8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 8:

GTCCTCGAGG AGGCGGCCGC ACCTCATCAA GTCTAT                36

(2) INFORMATION FOR SEQ ID NO: 9:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iii) ANTI-SENSE: NO (v) FRAGMENT TYPE: internal (xi) SEQUENCE DESCRIPTION: SEQ ID NO: 9:

Val Leu Glu Glu Ala Ala Ala Pro His Gln Val Tyr
1               5                   10

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 10:

GTAAGGTCAG GCCACCAGGT                                  20